US012576206B2

(12) United States Patent (10) Patent No.: US 12,576,206 B2
O'Connor et al. (45) Date of Patent: Mar. 17, 2026

(54) WEARABLE AUTOMATED MEDICATION DELIVERY SYSTEM

(71) Applicant: Insulet Corporation, Acton, MA (US)

(72) Inventors: Jason O'Connor, Acton, MA (US); Daniel Allis, Boxford, MA (US); David Nazzaro, Groveland, MA (US); John R. Bussiere, Littleton, MA (US); John D'Arco, Wilmington, MA (US)

(73) Assignee: INSULET CORPORATION, Acton, MA (US)

( * ) Notice: Subject to any disclaimer, the term of this patent is extended or adjusted under 35 U.S.C. 154(b) by 875 days.

(21) Appl. No.: 17/403,784

(22) Filed: Aug. 16, 2021

(65) Prior Publication Data

US 2021/0379282 A1 Dec. 9, 2021

Related U.S. Application Data

(63) Continuation of application No. 17/079,393, filed on Oct. 23, 2020, now Pat. No. 11,090,434, which is a
(Continued)

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *G16H 20/17* (2018.01);
(Continued)

(58) Field of Classification Search
None
See application file for complete search history.

(56) References Cited

U.S. PATENT DOCUMENTS 303,013 A 8/1884 Horton
311,735 A 2/1885 Fenner
(Continued)

FOREIGN PATENT DOCUMENTS

CA 2423717 A 4/2002
CN 1476566 A1 2/2004
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — GOODWIN PROCTER LLP

(57) ABSTRACT

Systems and methods for automatically delivering medication to a user. An automated drug delivery system may include a sensor and a wearable automated drug delivery device. The wearable automated drug delivery device may be configured to couple to the skin of a user and may include a controller and a pump. The pump may be configured to output the medication. The controller may be within the wearable automated drug delivery device. The sensor may be coupled to the user and may be configured to collect information regarding the user. The controller of the wearable automated drug delivery device may use the collected information to locally determine an amount of medication to be output from the wearable automated drug delivery device and cause delivery of the amount of medication.

20 Claims, 12 Drawing Sheets

Related U.S. Application Data continuation of application No. 16/898,529, filed on Jun. 11, 2020, now Pat. No. 11,744,944, which is a continuation of application No. 15/359,187, filed on Nov. 22, 2016, now Pat. No. 10,716,896.

(60) Provisional application No. 62/290,577, filed on Feb. 3, 2016, provisional application No. 62/259,143, filed on Nov. 24, 2015.

(51) Int. Cl.
　　*G16H 20/17* 　　　(2018.01)
　　*G16H 40/63* 　　　(2018.01)

(52) U.S. Cl.
　　CPC ......... *G16H 40/63* (2018.01); *A61M 2205/27* (2013.01); *A61M 2205/3569* (2013.01); *A61M 2205/3584* (2013.01); *A61M 2205/581* (2013.01); *A61M 2205/582* (2013.01); *A61M 2205/583* (2013.01); *A61M 2205/8206* (2013.01); *A61M 2230/201* (2013.01)

(56) References Cited

U.S. PATENT DOCUMENTS

| | | |
|---|---|---|
| 315,727 A | 4/1885 | Church |
| 405,524 A | 6/1889 | Bentor |
| 1,177,802 A | 4/1916 | Price |
| 3,631,847 A | 1/1972 | Hobbs |
| 3,812,843 A | 5/1974 | Wootten et al. |
| 3,885,662 A | 5/1975 | Schaefer |
| 3,923,426 A | 12/1975 | Theeuwes |
| 4,067,000 A | 1/1978 | Carlson |
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,265,241 A | 5/1981 | Portner et al. |
| 4,268,150 A | 5/1981 | Chen |
| 4,336,812 A | 6/1982 | Seragnoli |
| 4,342,311 A | 8/1982 | Whitney et al. |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,487,603 A | 12/1984 | Harris |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,598,719 A | 7/1986 | Mattei et al. |
| 4,600,020 A | 7/1986 | Mattei et al. |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,766,889 A | 8/1988 | Trick et al. |
| 4,781,688 A | 11/1988 | Thoma et al. |
| 4,781,693 A | 11/1988 | Martinez et al. |
| 4,791,942 A | 12/1988 | Rickett et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,893,640 A | 1/1990 | Heitmann et al. |
| 4,898,578 A | 2/1990 | Rubalcaba, Jr. |
| 4,898,579 A | 2/1990 | Groshong et al. |
| 4,924,885 A | 5/1990 | Heitmann et al. |
| 4,944,659 A | 7/1990 | Labbe et al. |
| 4,969,874 A | 11/1990 | Michel et al. |
| 4,973,998 A | 11/1990 | Gates |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,390,671 A | 2/1995 | Lord et al. |
| 5,411,480 A | 5/1995 | Kriesel |
| 5,414,732 A | 5/1995 | Kaufmann |
| 5,433,710 A | 7/1995 | VanAntwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. |
| 5,514,096 A | 5/1996 | Hiejima |
| 5,533,389 A | 7/1996 | Kamen et al. |
| 5,545,152 A | 8/1996 | Funderburk et al. |
| 5,551,953 A | 9/1996 | Lattin et al. |
| 5,569,186 A | 10/1996 | Lord et al. |
| 5,569,187 A | 10/1996 | Kaiser |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,586,553 A | 12/1996 | Halili et al. |
| 5,615,693 A | 4/1997 | Saitoh |
| 5,630,710 A | 5/1997 | Tune et al. |
| 5,637,095 A | 6/1997 | Nason et al. |
| 5,643,213 A | 7/1997 | McPhee |
| 5,645,085 A | 7/1997 | Mengoli et al. |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,740,817 A | 4/1998 | Cunningham |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |

(56)                    References Cited

U.S. PATENT DOCUMENTS

| | | | |
|---|---|---|---|
| 5,776,103 A | 7/1998 | Kriesel et al. | |
| 5,779,676 A | 7/1998 | Kriesel et al. | |
| 5,785,681 A | 7/1998 | Indravudh | |
| 5,785,688 A | 7/1998 | Joshi et al. | |
| 5,797,881 A | 8/1998 | Gadot | |
| 5,800,397 A | 9/1998 | Wilson et al. | |
| 5,800,405 A | 9/1998 | McPhee | |
| 5,800,420 A | 9/1998 | Gross et al. | |
| 5,807,375 A | 9/1998 | Gross et al. | |
| 5,810,015 A | 9/1998 | Flaherty | |
| 5,814,020 A | 9/1998 | Gross | |
| 5,839,467 A | 11/1998 | Saaski et al. | |
| 5,840,063 A | 11/1998 | Flaherty | |
| 5,845,218 A | 12/1998 | Altschul | |
| 5,848,991 A | 12/1998 | Gross et al. | |
| 5,851,197 A | 12/1998 | Marano et al. | |
| 5,858,005 A | 1/1999 | Kriesel | |
| 5,858,239 A | 1/1999 | Kenley et al. | |
| 5,865,806 A | 2/1999 | Howell | |
| 5,871,470 A | 2/1999 | McWha | |
| 5,875,393 A | 2/1999 | Altschul et al. | |
| 5,886,647 A | 3/1999 | Badger et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,931,814 A | 8/1999 | Alex et al. | |
| 5,935,099 A | 8/1999 | Peterson et al. | |
| 5,954,058 A | 9/1999 | Flaherty | |
| 5,957,890 A | 9/1999 | Mann et al. | |
| 5,957,895 A | 9/1999 | Sage et al. | |
| 5,961,492 A | 10/1999 | Kriesel et al. | |
| 5,965,848 A | 10/1999 | Altschul et al. | |
| 5,983,094 A | 11/1999 | Altschul et al. | |
| 5,983,136 A | 11/1999 | Kamen | |
| 5,984,894 A | 11/1999 | Poulsen et al. | |
| 5,993,423 A | 11/1999 | Choi | |
| 5,997,501 A | 12/1999 | Gross et al. | |
| 6,019,747 A | 2/2000 | McPhee | |
| 6,024,539 A | 2/2000 | Blomquist | |
| 6,050,457 A | 4/2000 | Arnold et al. | |
| 6,061,580 A | 5/2000 | Altschul et al. | |
| 6,071,292 A | 6/2000 | Makower et al. | |
| 6,144,847 A | 11/2000 | Altschul et al. | |
| 6,152,898 A | 11/2000 | Olsen | |
| 6,159,188 A | 12/2000 | Laibovitz et al. | |
| 6,171,264 B1 | 1/2001 | Bader | |
| 6,174,300 B1 | 1/2001 | Kriesel et al. | |
| 6,190,359 B1 | 2/2001 | Heruth | |
| 6,206,850 B1 | 3/2001 | ONeil | |
| 6,244,776 B1 | 6/2001 | Wiley | |
| 6,363,609 B1 | 4/2002 | Pickren | |
| 6,375,638 B2 | 4/2002 | Nason et al. | |
| 6,427,088 B1 | 7/2002 | Bowman, IV et al. | |
| 6,485,462 B1 | 11/2002 | Kriesel | |
| 6,520,936 B1 | 2/2003 | Mann | |
| 6,527,744 B1 | 3/2003 | Kriesel et al. | |
| 6,554,798 B1 | 4/2003 | Mann et al. | |
| 6,558,320 B1 | 5/2003 | Causey, III et al. | |
| 6,572,585 B2 | 6/2003 | Choi | |
| 6,641,533 B2 | 11/2003 | Causey, III et al. | |
| 6,645,142 B2 | 11/2003 | Braig et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,689,091 B2 | 2/2004 | Bui et al. | |
| 6,692,457 B2 | 2/2004 | Flaherty | |
| 6,723,072 B2 | 4/2004 | Flaherty et al. | |
| 6,740,059 B2 | 5/2004 | Flaherty | |
| 6,749,587 B2 | 6/2004 | Flaherty | |
| 6,768,425 B2 | 7/2004 | Flaherty et al. | |
| 6,809,653 B1 | 10/2004 | Mann et al. | |
| 6,960,192 B1 | 11/2005 | Flaherty et al. | |
| 7,018,360 B2 | 3/2006 | Flaherty et al. | |
| 7,029,455 B2 | 4/2006 | Flaherty | |
| 7,083,593 B2 | 8/2006 | Stultz | |
| 7,128,727 B2 | 10/2006 | Flaherty et al. | |
| 7,137,964 B2 | 11/2006 | Flaherty | |
| 7,144,384 B2 | 12/2006 | Gorman et al. | |
| 7,303,549 B2 | 12/2007 | Flaherty et al. | |
| 7,727,147 B1 * | 6/2010 | Osorio | A61M 5/14244 |
| | | | 600/347 |
| 7,887,505 B2 | 2/2011 | Flaherty | |
| 7,887,511 B2 | 2/2011 | Mernøe et al. | |
| 8,140,275 B2 | 3/2012 | Campbell et al. | |
| 8,622,954 B2 | 1/2014 | Shahmirian et al. | |
| 8,663,101 B2 | 3/2014 | Calvosa et al. | |
| 8,663,103 B2 | 3/2014 | Causey, III et al. | |
| 9,813,985 B2 | 11/2017 | Shapley et al. | |
| 10,046,114 B1 | 8/2018 | Biederman et al. | |
| 10,064,992 B2 | 9/2018 | Yang | |
| 10,448,885 B2 | 10/2019 | Schmid | |
| 2001/0056258 A1 | 12/2001 | Evans | |
| 2002/0016568 A1 | 2/2002 | Lebel et al. | |
| 2002/0019606 A1 | 2/2002 | Lebel et al. | |
| 2002/0040208 A1 | 4/2002 | Flaherty et al. | |
| 2002/0065454 A1 | 5/2002 | Lebel et al. | |
| 2002/0107476 A1 | 8/2002 | Mann et al. | |
| 2002/0123740 A1 | 9/2002 | Flaherty et al. | |
| 2002/0126036 A1 | 9/2002 | Flaherty et al. | |
| 2002/0169416 A1 | 11/2002 | Gonnelli et al. | |
| 2003/0055406 A1 | 3/2003 | Lebel et al. | |
| 2003/0065308 A1 | 4/2003 | Lebel et al. | |
| 2003/0088238 A1 | 5/2003 | Poulsen et al. | |
| 2003/0212379 A1 | 11/2003 | Bylund et al. | |
| 2003/0217755 A1 | 11/2003 | Koch et al. | |
| 2004/0010207 A1 | 1/2004 | Flaherty et al. | |
| 2004/0010507 A1 | 1/2004 | Bellew | |
| 2004/0068224 A1 | 4/2004 | Couvillon, Jr. et al. | |
| 2004/0092865 A1 | 5/2004 | Flaherty et al. | |
| 2004/0122489 A1 | 6/2004 | Mazar et al. | |
| 2004/0260233 A1 | 12/2004 | Garibotto et al. | |
| 2005/0171512 A1 | 8/2005 | Flaherty | |
| 2005/0238507 A1 | 10/2005 | Dilanni et al. | |
| 2006/0282290 A1 | 12/2006 | Flaherty et al. | |
| 2006/0292987 A1 | 12/2006 | Ophir et al. | |
| 2007/0112298 A1 | 5/2007 | Mueller et al. | |
| 2007/0118405 A1 | 5/2007 | Campbell et al. | |
| 2007/0142748 A1 * | 6/2007 | Deshmukh | A61B 5/150251 |
| | | | 600/583 |
| 2007/0281617 A1 | 12/2007 | Meylan et al. | |
| 2009/0048556 A1 | 2/2009 | Durand | |
| 2009/0062767 A1 | 3/2009 | Van Antwerp et al. | |
| 2009/0076359 A1 | 3/2009 | Peyser | |
| 2009/0112769 A1 | 4/2009 | Dicks et al. | |
| 2010/0137784 A1 | 6/2010 | Cefai et al. | |
| 2011/0009824 A1 | 1/2011 | Yodfat et al. | |
| 2011/0047499 A1 | 2/2011 | Mandro et al. | |
| 2011/0071765 A1 | 3/2011 | Yodfat et al. | |
| 2011/0093286 A1 | 4/2011 | Dicks et al. | |
| 2011/0118578 A1 | 5/2011 | Timmerman | |
| 2011/0118694 A1 | 5/2011 | Yodfat et al. | |
| 2011/0124996 A1 | 5/2011 | Reinke et al. | |
| 2011/0257496 A1 | 10/2011 | Terashima et al. | |
| 2011/0316562 A1 | 12/2011 | Cefai et al. | |
| 2012/0029941 A1 | 2/2012 | Malave et al. | |
| 2012/0182939 A1 | 7/2012 | Rajan et al. | |
| 2012/0266251 A1 | 10/2012 | Birthwhistle et al. | |
| 2012/0277667 A1 | 11/2012 | Yodat et al. | |
| 2014/0039383 A1 | 2/2014 | Dobbles et al. | |
| 2014/0148779 A1 | 5/2014 | Rao et al. | |
| 2014/0180203 A1 | 6/2014 | Budiman et al. | |
| 2014/0309615 A1 | 10/2014 | Mazlish | |
| 2015/0038898 A1 | 2/2015 | Palmer et al. | |
| 2015/0057634 A1 | 2/2015 | Mastrototaro et al. | |
| 2015/0057807 A1 | 2/2015 | Mastrototaro et al. | |
| 2015/0119666 A1 | 4/2015 | Brister et al. | |
| 2015/0164390 A1 | 6/2015 | Larvenz et al. | |
| 2015/0173674 A1 | 6/2015 | Hayes et al. | |
| 2015/0217052 A1 | 8/2015 | Keenan et al. | |
| 2015/0366945 A1 | 12/2015 | Greene | |
| 2016/0183794 A1 | 6/2016 | Gannon et al. | |
| 2017/0100536 A1 | 4/2017 | Estes | |

(56) References Cited

U.S. PATENT DOCUMENTS

| 2017/0112531 | A1 | 4/2017 | Schoonmaker et al. |
|---|---|---|---|
| 2017/0117622 | A1 | 4/2017 | Backman et al. |
| 2018/0008770 | A1 | 1/2018 | Savoie et al. |
| 2018/0075200 | A1 | 3/2018 | Davis et al. |
| 2018/0307515 | A1 | 10/2018 | Meller et al. |
| 2019/0117133 | A1 | 4/2019 | Halac et al. |
| 2019/0132801 | A1 | 5/2019 | Kamath et al. |
| 2019/0150805 | A1 | 5/2019 | Routh et al. |
| 2019/0321545 | A1 | 10/2019 | Saint |
| 2020/0037939 | A1 | 2/2020 | Castagna et al. |
| 2020/0147304 | A1 | 5/2020 | Crouther et al. |

FOREIGN PATENT DOCUMENTS

| DE | 4200595 | A1 | 7/1993 | | |
|---|---|---|---|---|---|
| DE | 19920896 | A1 | 11/2000 | | |
| EP | 0319272 | A2 | 6/1989 | | |
| EP | 0342947 | A2 | 11/1989 | | |
| EP | 0755636 | A1 | 1/1997 | | |
| EP | 0763369 | A1 | 3/1997 | | |
| EP | 0867196 | A2 | 9/1998 | | |
| EP | 0937475 | A2 | 8/1999 | | |
| EP | 1177802 | A1 | 2/2002 | | |
| EP | 1364588 | A1 | 11/2003 | | |
| WO | 8101658 | A1 | 6/1981 | | |
| WO | 8606796 | A1 | 11/1986 | | |
| WO | 9800193 | A1 | 1/1998 | | |
| WO | 9801071 | A1 | 1/1998 | | |
| WO | 9841267 | A1 | 9/1998 | | |
| WO | 9910040 | A1 | 3/1999 | | |
| WO | 9910049 | A1 | 3/1999 | | |
| WO | 9956803 | A1 | 11/1999 | | |
| WO | 9962576 | A1 | 12/1999 | | |
| WO | 0010628 | A2 | 3/2000 | | |
| WO | 0013580 | A1 | 3/2000 | | |
| WO | 0019887 | A1 | 4/2000 | | |
| WO | 0029047 | A1 | 5/2000 | | |
| WO | 0029049 | A1 | 5/2000 | | |
| WO | 0030705 | A1 | 6/2000 | | |
| WO | 0048112 | A2 | 8/2000 | | |
| WO | 0061215 | A1 | 10/2000 | | |
| WO | 0074752 | A1 | 12/2000 | | |
| WO | 0078210 | A1 | 12/2000 | | |
| WO | 0152727 | A1 | 7/2001 | | |
| WO | 0015663 | A1 | 8/2001 | | |
| WO | 0156633 | A2 | 8/2001 | | |
| WO | 0176684 | A1 | 10/2001 | | |
| WO | 0220073 | A2 | 3/2002 | | |
| WO | 0226282 | A2 | 4/2002 | | |
| WO | 2003090509 | | 11/2003 | | |
| WO | 2004041330 | A2 | 5/2004 | | |
| WO | WO-2011028278 | A1 * | 3/2011 | ........ | A61M 25/0009 |
| WO | 2014136105 | A1 | 9/2014 | | |

OTHER PUBLICATIONS

International Search Report and Written Opinion for the International Patent Application No. PCT/US2021/064041, mailed Apr. 29, 2022, 11 pages.

International Search Report and Written Opinion for the International Patent Application No. PCT/US2022/013139, mailed May 18, 2022, 12 pages.

International Search Report and Written Opinion for the International Patent Application No. PCT/US2021/063918, mailed May 30, 2022, 10 pages.

International Search Report for International Patent Application No. PCT/US03/28769, mailed Jun. 23, 2004, 1 page.

International Search Report for International Application No. PCT/US02/28053, mailed May 20, 2003, 1 page.

International Search Report for International Application No. PCT/US03/03731, mailed Jul. 2, 2003, 2 pages.

International Search Report for International Patent Application No. PCT/US01/51285, mailed Nov. 11, 2002.

International Search Report for International Patent Application No. PCT/US03/29019, mailed Aug. 2, 2004, 1 page.

International Search Report and Written Opinion for the International Patent Application No. PCT/US21/064056, mailed Apr. 4, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

International Search Report and Written Opinion for the International Patent Application No. PCT/US2021/063914, mailed Apr. 13, 2022, 11 pages.

International Search Report for the International Patent Application No. PCT/US16/63420, mailed Mar. 29, 2017, 9 pages.

International Search Report for the International Patent Application No. PCT/US01/31089, dated May 16, 2002, 3 pages.

International Search Report for the International Patent Application No. PCT/US01/50581, dated Sep. 30, 2002, 3 pages.

Preliminary Report on Patentability mailed Dec. 21, 2017, issued in PCT International Patent Application No. PCT/US2016/037189, 12 pages.

PCT Search Report and Written Opinion mailed Sep. 9, 2016, received in corresponding PCT Application No. PCT/US16/37189, 12 pgs.

International Search Report for the International Patent Application No. PCT/US03/12370, dated Dec. 15, 2003, 1 page.

Web-Site Brochure dated Jan. 4, 2000. MiniMed 508. "Doing its job. Naturally." www.minimed.com/tiles/mm_113.htm.

Web-site Brochure dated Dec. 20, 1999. Applied Medical Technology. "508 Pump Information". Www.applied-medical.co.uk/508.htm.

Web-Site Brochure dated Jan. 4, 2000. "The Glucose Sensor". Www.animascorp.com/sensor_f.html.

Web-Site Brochure dated Dec. 20, 1999. "The Animas R-1000 Insulin Pump". Www.animascorp.com/pump_f_s.html.

Web-Site Brochure dated Dec. 20, 1999. "The Animas R-1000 Insulin Pump". Www.animascorp.com/pump_f_f.html.

Web-site Brochure dated Jan. 4, 2000. SOOIL-Homepage. "Portable Insulin Pump". Www.sooil.com/intro2.htm.

Web-Site Brochure dated Jan. 4, 2000. SOOIL-Homepage. "Portable Insulin Pump". Www.sooil.com/product2.htm.

Web-Site Brochure dated Jan. 4, 2000. SOOIL-Homepage. "Portable Insulin Pump". Www.sooil.com/product3.htm.

Web-Site Brochure dated Jan. 4, 2000. SOOIL-Homepage. "Portable Insulin Pump". Www.sooil.com/product4.htm.

User's Guide for Model 508 Insulin Pump, MiniMed, Aug. 2000, 145 pages.

PCT International Search Report dated Mar. 4, 2002; 5pp.

International Search Report for the International Patent Application No. PCT/GB2015/050249, dated Jul. 7, 2015, 18 pages.

PCT/US04/13804 International Search Report and Written Opinion (Nov. 18, 2004).

International Preliminary Examining Authority, International SearchReport PCT/US02/28053, May 20, 2003.

Communication Pursuant to Article 96(2) EPC EPA No. 01968320.0 (Jan. 21, 2005).

Communication Pursuant to Article 96(2) EPC EPA No. 01977472.8 (Jul. 19, 2004).

Communication Pursuant To Article 96(2) EPC EPA No. 01987579.8 (Jan. 26, 2005).

International Preliminary Examining Authority, International Preliminary Examination Report PCT/US03/28769, Aug. 12, 2004.

International Preliminary Examining Authority, International Search Report PCT/US03/29019, Aug. 2, 2004.

International Preliminary Examining Authority, International Preliminary Examination Report PCT/US03/09952, Jan. 20, 2004.

International Preliminary Examining Authority, International Preliminary Examination Report PCT/US03/12370, Dec. 15, 2003.

International Preliminary Examining Authority, International Preliminary Examination Report PCT/US03/12370, Feb. 11, 2004.

International Preliminary Examining Authority, International Preliminary Examination Report PCT/US03/16545, Feb. 23, 2004.

(56) References Cited

OTHER PUBLICATIONS

International Preliminary Examining Authority, International Search Report PCT/US01/31089, May 20, 2002.

International Preliminary Examining Authority, International Search Report PCT/US02/30803, Mar. 3, 2003.

International Preliminary Examining Authority, International Search Report PCT/US03/09952, Aug. 12, 2003.

International Preliminary Examining Authority, International Search Report PCT/US03/16545, Oct. 6, 2003.

International Preliminary Examining Authority, International Search Report PCT/US03/19756, Mar. 10, 2004.

International Searching Authority, International Preliminary Examination Report PCT/US03/16640, Feb. 25, 2004.

International Searching Authority, International Search Report PCT/US01/51285, Jun. 11, 2002.

International Searching Authority, International Search Report PCT/US03/16640, Oct. 2, 2003.

International Preliminary Examining Authority, International Preliminary Examination Report PCT/US03/09606, Dec. 16, 2003.

International Preliminary Examining Authority, International Preliminary Examination Report PCT/US01/10933, Oct. 28, 2003.

International Preliminary Examining Authority, International Preliminary Examination Report PCT/US01/27108, Nov. 4, 2003.

International Preliminary Examining Authority, International Preliminary Examination Report PCT/US02/05338, Mar. 3, 2003.

International Preliminary Examining Authority, International Preliminary Examination Report PCT/US02/28053, Dec. 9, 2004.

International Preliminary Examining Authority, International Search Report PCT/US01/10933, Oct. 28, 2003.

International Preliminary Examining Authority, International Search Report PCT/US01/27108, Apr. 3, 2002.

International Preliminary Examining Authority, International Search Report PCT/US02/05338, Dec. 18, 2002.

International Preliminary Examining Authority, International Search Report PCT/US03/03731, Jul. 2, 2003.

International Preliminary Examining Authority, International Search Report PCT/US03/09606, Oct. 20, 2003.

* cited by examiner

400

Receive, from an electronic device, a
wireless command for an action associated
with delivering medication          402

Receive user input from a person wearing a
medical device confirming the action          404

Executing the action associated with
delivering the medication only if the user
input confirming the action is received          406

WEARABLE AUTOMATED MEDICATION DELIVERY SYSTEM

CROSS-REFERENCE TO RELATED APPLICATIONS

This application is a continuation of U.S. patent application Ser. No. 17/079,393, filed Oct. 23, 2020, which is a continuation of U.S. patent application Ser. No. 16/898,529, filed Jun. 11, 2020, which is a continuation of U.S. patent application Ser. No. 15/359,187 (now U.S. Pat. No. 10,716, 896), filed Nov. 22, 2016, which claims priority to U.S. Provisional Patent Application No. 62/259,143, filed Nov. 24, 2015, and to U.S. Provisional Patent Application No. 62/290,577, filed Feb. 3, 2016, the entirety of which are hereby incorporated by reference.

TECHNICAL FIELD

Embodiments herein generally relate to automated medication delivery and, more particularly, to wireless medication delivery systems using wearable medication delivery devices.

BACKGROUND

"Artificial pancreas" systems can be medication delivery systems that typically monitor a user's glucose levels, determine an appropriate level of insulin for the user based on the monitored glucose levels, and subsequently dispense the insulin to the user. Sophisticated control algorithms needed for these systems generally require powerful computing resources and significant power resources. As a result, conventional medication delivery systems do not provide for wireless communications between system components, fully autonomous operation, enhanced user experiences involving ubiquitous electronic devices like cellphones, and improved security features. A need therefore exists for an insulin management system that includes such features.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Various embodiments of the present invention include systems and methods for delivering a medication to a person using a wearable medical device in accordance with a wireless signal received from an electronic device. In various embodiments, the electronic device is a smart watch, smart necklace, module attached to the medical device, or any other type or sort of electronic device that may be worn or carried on the body of the person and executes an algorithm that computes the times and dosages of delivery of the medication. For example, the electronic device may execute an artificial-pancreas algorithm that computes the times and dosages of delivery of insulin. The electronic device may also be in communication with a sensor, such as a glucose sensor, that collects data on a physical attribute or condition of the person, such as a glucose level. The sensor may be disposed in or on the body of the person and may be part of the medical device or may be a separate device. Alternately, the medical device may be in communication with the sensor in lieu of or in addition to the communication between the sensor and the electronic device. The communication may be direct (if, e.g., the sensor is integrated with or otherwise a part of the medical device) or remote/wireless (if, e.g., the sensor is disposed in a different housing than the medical device). In these embodiments, the sensor and/or medical device contains computing hardware (e.g., a processor, memory, firmware, etc.) that executes some or all of the algorithm that computes the times and dosages of delivery of the medication.

Various embodiments described herein include systems and methods for automatically delivering medication to a user. A sensor coupled to a user can collect information regarding the user. A controller can use the collected information to determine an amount of medication to provide the user. The controller can instruct a drug delivery device to dispense the medication to the user. The drug delivery device can be a wearable insulin pump that is directly coupled to the user. The controller can be part of or implemented in a cellphone. A user can be required to provide a confirmation input to allow a determined amount of insulin to be provided to the user based on detected glucose levels of the user.

Figure 1A:
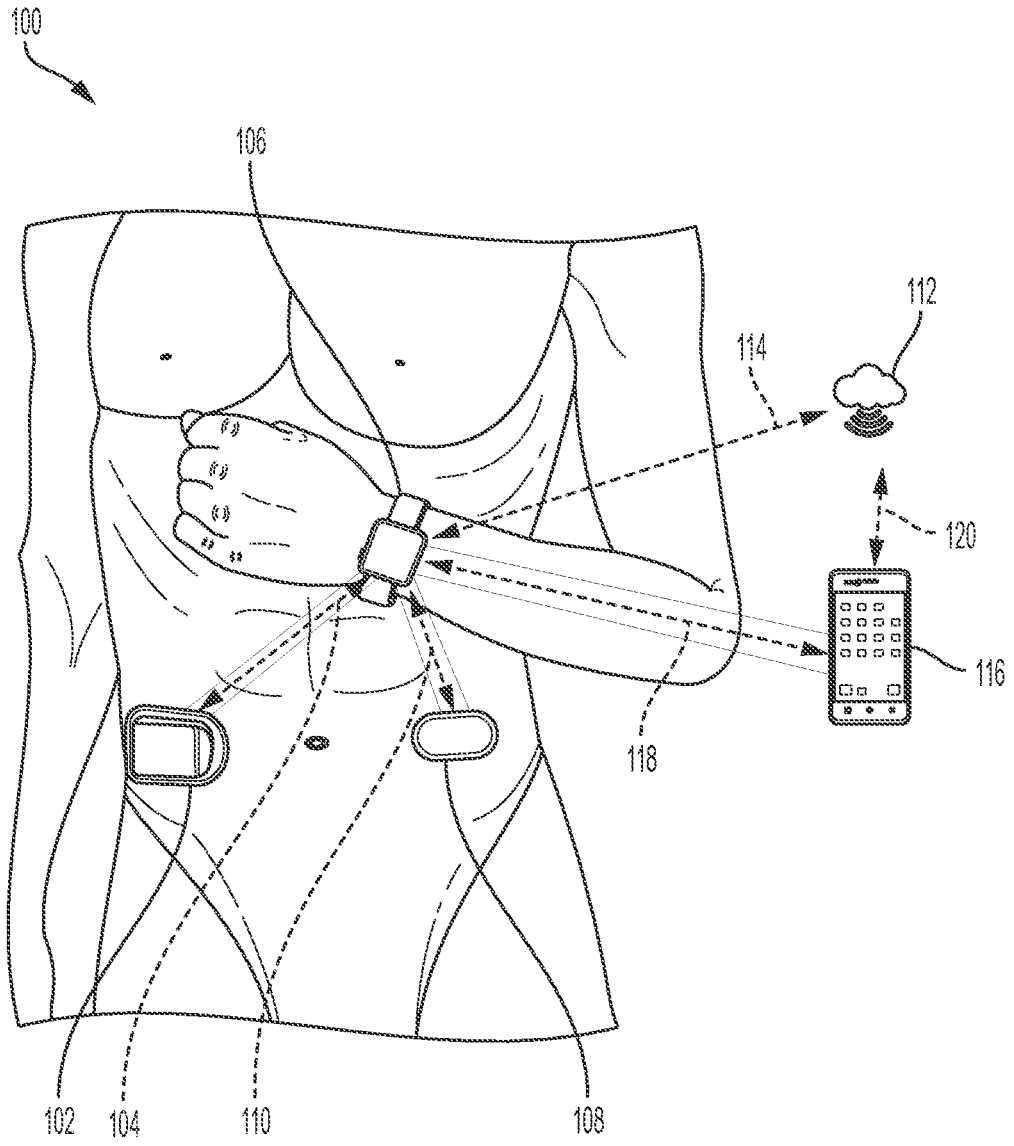
FIG. 1A illustrates a first exemplary wearable automated medication delivery system.

FIG. 1A illustrates a first exemplary wearable automated medication delivery system 100. The wearable automated medication delivery system 100 can include a medical device 102. The medical device 102 can be attached to the body of a user and can deliver a medication to the user. The medical device 102 can be a wearable device. In particular, the medical device 102 can be directly coupled to a user (e.g., directly attached to a body part and/or skin of the user). A surface of the medical device 102 can include an adhesive to facilitate attachment to the user.

The medical device 102 can include a number of components to facilitate automated delivery of a medication to the user. For example, the medical device 102 can include a reservoir for storing the medication, a needle or cannula for delivering the medication into the body of the person, and a pump for transferring the medication from the reservoir, through the needle or cannula, into the body of the user. The medical device 102 can also include a power source such as a battery for supplying power to the pump and/or other components of the medical device 102.

The medical device 102 can store and provide any medication or drug to the user. In various embodiments, the medical device 102 can be an automated wearable insulin delivery device. For example, the medical device 102 can be the OmniPod® (Insulet Corporation, Billerica, MA) insulin delivery device as described in U.S. Pat. Nos. 7,303,549, 7,137,964, or 6,740,059, each of which is incorporated herein by reference in its entirety.

The medical device 102 may include a housing, an exit port, disposed in a first wall of the housing for enabling a cannula to penetrate the skin of a patient (i.e., user). The cannula may be in the form of a rigid hollow needle having a penetrating portion, such as a sharpened point of the cannula for penetrating the skin of the person upon deployment of the cannula as described below.

The medical device 102 may further include a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device. The fluid transport device includes a needle housed within a flexible cannula, the penetrating member being disposed at a distal end of the needle, beyond a distal end of the flexible cannula, the flexible cannula having a length that is less than a length of the needle, wherein a proximal end of the flexible cannula, opposite the distal end of the needle, is constructed and arranged to provide a frictional seal between the flexible cannula and the needle, the frictional seal preventing an escape of the fluid from between the distal end of the cannula and the needle, while allowing the distal end of the cannula to slide along the needle. An injection activation device includes a plunger coupled to the fluid transport device, such that the application of a first force in a first direction to the plunger drives the fluid transport device from a first position to a second position. The penetrating member of the needle and the distal end of the flexible cannula may extend through the exit port and into the skin of the person.

In an alternative embodiment described in more detail below, a needle insertion device may include or be configured as an actuator that may be used to inject the cannula into the skin of the person, and the actuator may include electronics and wireless receiver separate from a primary housing of the medical device 102 to enable the primary housing of the medical device to have a smaller size and to enable the overall cost of the medical device to be greatly reduced. The actuator is attachable to the housing for deployment of the cannula into the skin of the user and can be removed for use with another medical device. The octuator may include a latch mechanism including a latch and a deployment lever. The latch may be spring biased such that a protrusion is in contact with latch, thereby preventing the plunger device from deploying.

The latch release mechanism may include an electrically driven actuator coupled between the latch and the side wall of the housing, such that, upon the application of a charge to the electrically driven actuator, the electrically driven actuator activates to pull the latch out of contact with the distal end of the pivoting arm. The electrically driven actuator may include one of a shape memory alloy, a shape memory polymer, a piezo electric actuator and a solenoid. The medical device may further include a local processor connected to the latch release mechanism and programmed to apply a charge to the electrically driven actuator based on injection instructions; and a wireless receiver connected to the local processor for receiving injection instructions from a separate, remote control device and delivering the needle/cannula injection instructions to the local processor. The housing may be free of user input components for providing injection instructions to the local processor. The system may further include a remote control device separate from the medical device (i.e., a wearable drug delivery device or automatic drug delivery device), the remote control device including a remote processor; user interface components connected to the remote processor for transmitting the needle/cannula injection instructions and a transmitter connected to the remote processor for transmitting the needle/cannula injection instructions to the receiver of the medical device.

In another example, the latch release mechanism may include an electrically driven actuator coupled between the latch and the housing, such that, upon the application of a charge to the electrically driven actuator, a shape memory alloy wire may contract to pull the latch out of contact with a lateral protrusion of the fluid transport device. The electrically driven actuator may include one of a shape memory alloy wire, a shape memory polymer, a piezo electric actuator and a solenoid. The device may further include a local processor connected to the latch release mechanism and programmed to apply a charge to the electrically driven actuator based on injection instructions and a wireless receiver connected to the local processor for receiving injection instructions from a separate, remote control device and delivering the injection instructions to the local processor.

The medical device 102 can also contain analog and/or digital circuitry for controlling the delivery of the medication. The circuitry can be implemented as a controller. The circuitry can include discrete, specialized logic and/or components, an application-specific integrated circuit, a microcontroller or processor that executes software instructions, firmware, or any combination thereof. In various embodiments, the control circuitry can be configured to cause the pump to deliver doses of the medication to the person at predetermined intervals. The size and/or timing of the doses may be programmed into the control circuitry using a wired or wireless link by the user or by a third party (such as a health care provider).

Instructions for determining the delivery of the medication to the user (e.g., the size and/or timing of any doses of the medication) can originate locally (e.g., based on determinations made by the medical device 102) or can originate remotely and then provided to the medical device 102. Remote instructions can be provided to the medical device 102 over a wired or wireless link. The medical device 102 can execute any received instructions for the delivery of the medication to the user. In this way, under either scenario, the delivery of the medication to the user can be automated.

In various embodiments, the medical device 102 can communicate via a wireless link 104 with an electronic device 106. The electronic device 106 can be any electronic device such as, for example, an Apple® Watch. The electronic device 106 can be a wearable wireless accessory device. The wireless link 104 can be any type of wireless link provided by any known wireless standard. As an example, the wireless link can provide communications based on Bluetooth®, Wi-Fi, a near-field communication standard, a cellular standard, or any other wireless protocol.

Figure 1B:
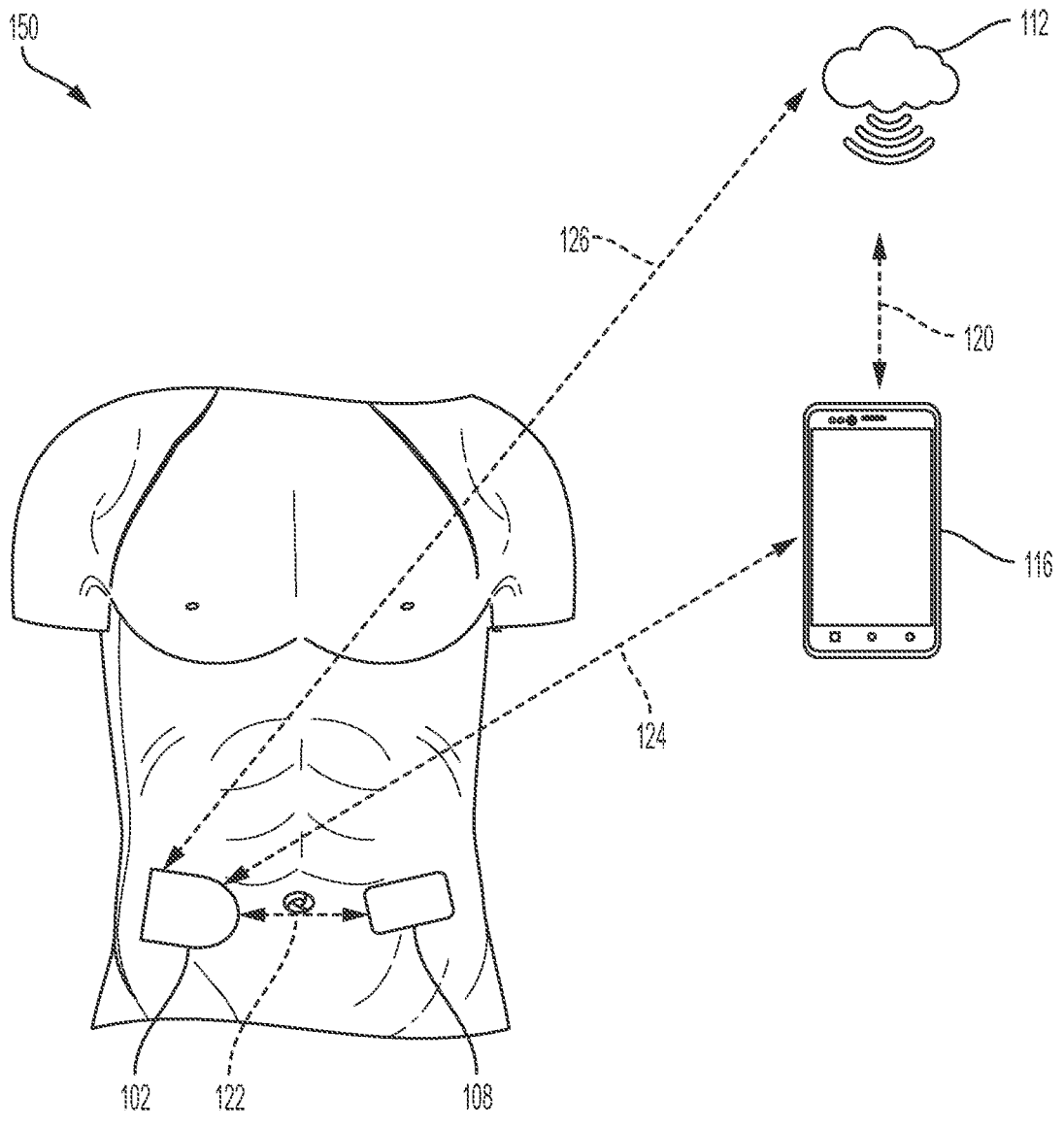
FIG. 1B illustrates a second exemplary wearable automated medication delivery system.

FIG. 1B illustrates a second exemplary wearable automated medication delivery system 150. The wearable automated medication delivery system 150 can also include the medical device 102. As shown in FIG. 1B, the medical device 102 can communicates via a wireless link 122 with a sensor 108. The wireless link 122 can be the same type of communication link as the link 104 in that it can provide wireless communications over any known wireless protocol or standard.

The control circuitry in the medical device 102 may include circuitry implementing a wireless transmitter, receiver, and/or transceiver for communication over the link 104 or 122. Information may be transmitted between the medical device 102 and the electronic device 106 over the link 104 and/or between the medical device 102 and the sensor 108 over the link 122. The shared information may include handshake/pairing information, data, commands, status information, or any other such information. In various embodiments, the electronic device 106 transmits a command to the medical device 102 that specifies an action for the medical device 102 to take regarding delivery of the medication. In another embodiment, the sensor 108 sends a signal to the medical device 102 via the link 122, and the medical device 102 executes an algorithm to determine an action for the medical device 102 to take regarding delivery of the medication. The action may be delivery of a bolus of the medication, a change in a time, frequency, or schedule of future deliveries of the medication, a change in a size of future deliveries of the medication, or any other such action. The command may further comprise a bolus size, a bolus time, or any other such additional information. The medical device 102 may transmit a confirmation message back to the electronic device 106 upon receipt of the command and/or after completion of the action.

The medical device 102 may include a power supply, such as a battery and/or capacitor, for supplying power to the pump and/or other components of the medical device 102. The power supply may be integrated into the medical device 102, but can be provided as replaceable, e.g., a replaceable battery.

In various embodiments, the electronic device 106 transmits the command as specified by an algorithm executing thereon, such as an artificial-pancreas algorithm. The algorithm may execute in the context of a software application running on the electronic device. The user may download this application from an application store, such as the Apple® iTunes® store, or from any other source. The algorithm may be used to compute appropriate times and doses of delivery of the medication. In some embodiments, the algorithm bases these computations at least in part on information known about the person, such as sex, age, weight, or height, and/or on information gathered about a physical attribute or condition of the person (e.g., from the sensor 108). For example, the algorithm may determine an appropriate delivery of the medication based on glucose level monitoring of the user. The software application may further permit the person to access status information regarding the medical device 102, such as its battery level, number of doses remaining, amount of time in use, or other such status information. The software application may instead or in addition allow the person to issue commands to the medical device 102, such as a command to deliver a bolus.

In various embodiments, as shown in FIGS. 1A and 1B, the sensor 108 is worn on the body of the person or implanted within the person and is used to collect information regarding one or more physical attributes or conditions of the person. The sensor 108 can be coupled to the user and worn on a body part of the user. The sensor 108 can be a glucose sensor. For example, the sensor 108 can be a continuous glucose monitor (CGM). Although the sensor 108 is depicted as separate from the medical device 102, in various embodiments, the sensor 108 and medical device 102 may be incorporated into the same unit. That is, in various embodiments, the sensor 108 can be a part of the medical device 102 and contained within the same housing of the medical device 102 (e.g., the sensor 108 can be positioned within or embedded within the medical device).

The sensor 108 can include one or more sensing elements, an electronic transmitter, receiver, and/or transceiver for communicating with the electronic device 106 over a link 110 or with medical device 102 over the link 122. The link 110 can be the same type of wireless link as the links 104 or 122. The sensor 108 can also include a power source for supplying power to the sensing elements and/or transceiver. Communications provided by the sensor 108 may include data gathered from the sensing elements. This data can be transmitted continually, at periodic intervals, and/or during or after a change in sensed data (e.g., if a glucose level or rate of change in the level exceeds a threshold). The software application executing the algorithm may use this collected information to send a command to the medical device 102 to, for example, deliver a bolus to the person, change the amount or timing of future doses, or other commands.

The electronic device 106 can be considered to be a wireless accessory device or an intermediate device. In various embodiments, the electronic device 106 can relay commands for delivery of a medication from a remote source to the medical device 102. In various embodiments, the electronic device 106 can include a controller for determining delivery of the medication (e.g., the electronic device can include a controller for executing an "artificial pancreas" algorithm). The electronic device 106 can also relay sensor data from the sensor 108 to the medical device 102. In general, the electronic device 106 can relay communications between any of the devices depicted in FIGS. 1A and 1B (e.g., communications in any direction between any two devices depicted).

The sensor 108 can be any type of sensor and is not limited to a CGM. The sensor 108 can include one or more sensors housed in the same physical unit.

The electronic device 106 and/or the medical device 102 may communicate with one or more remote devices 112, which may include computers, servers, storage devices, cloud-based services, or other similar devices. The remote device 112 may be owned or operated by, for example, health-care companies or services, pharmacies, doctors, nurses, or other such medically-related entities. The remote device 112 may include a cloud-based data management system. A user may wish, for example, to back up data collected from the sensor 108, back up a record of medication delivery times and doses provided by the medical device 102, or back up other such information. A wireless link 114 may be used to connect the electronic device 106 to the remote devices 112 and/or a wireless link 126 may be used to connect the medical device 102 to the remote devices 112. The wireless links 114 and 126 can be of the same type as the other wireless links described herein.

Alternatively, or in addition thereto, the electronic device 106 may communicate with a local device 116. The local device 116 can be a dedicated control or monitoring device (e.g., a diabetes management device and/or a custom handheld electronic computing device), cellular phone, laptop computer, tablet, desktop computer, or other similar electronic computing device. The local device 116 can communicate with the electronic device 106 over a wireless link 118. The wireless link 118 can be of the same type as the other wireless links described herein.

A software application executing on the local device 116 may be used to send commands to the medical device 102 (e.g., via the electronic device 106) and/or receive status information about the medical device 102 (e.g., via the electronic device 106). In other embodiments, the local device 116 instead or in addition communicates directly via a wireless link 124 with the medical device 102. The wireless link 124 can be of the same type as the other wireless links described herein.

Additionally, the sensor 108 may communicate via a wireless link with the local device 116. The local device 116 may communicate with the remote devices 112 via a wireless link 120. The wireless link 120 can be of the same type as the other wireless links described herein.

Figure 2:
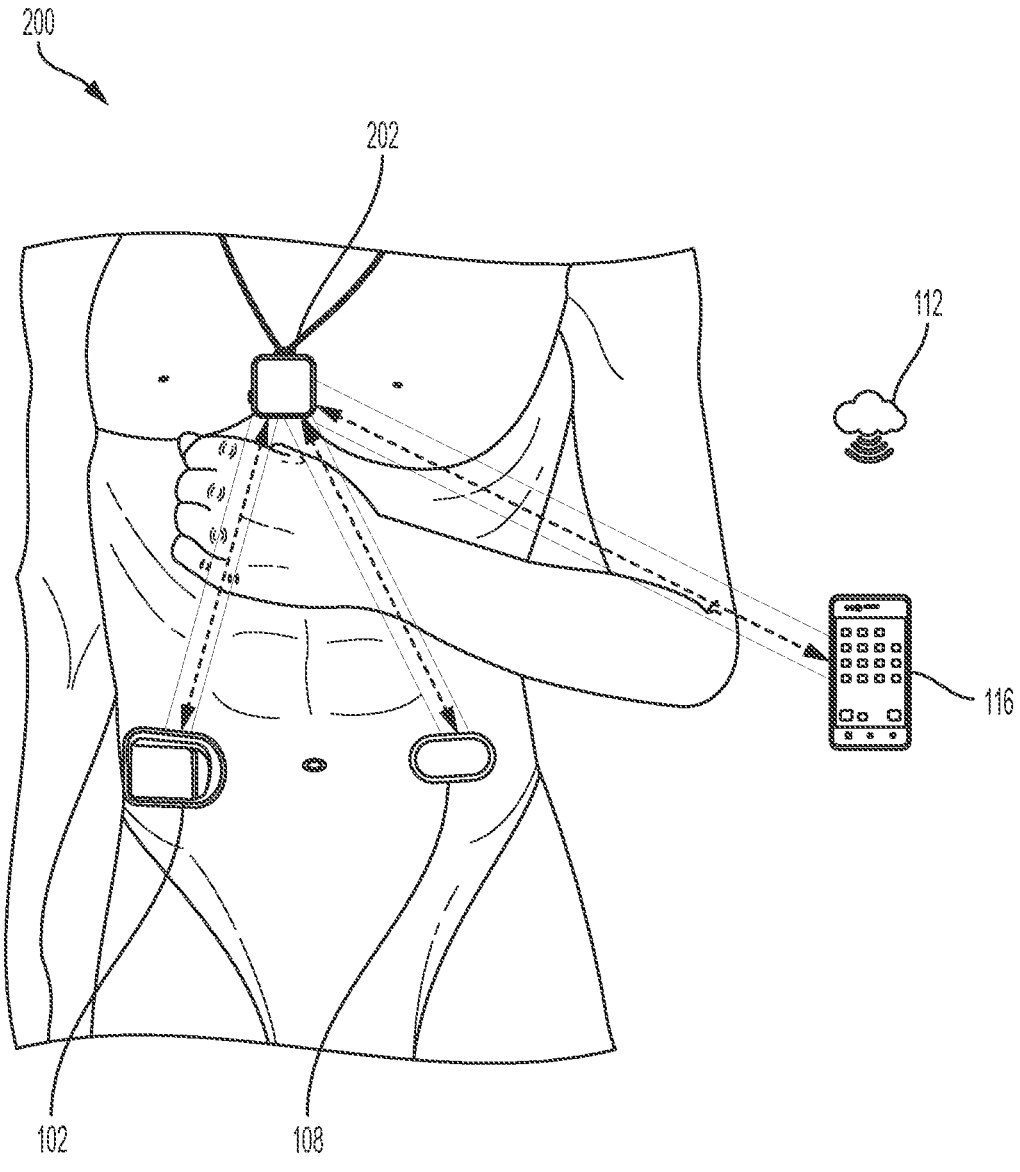
FIG. 2 illustrates a third exemplary wearable automated medication delivery system.

FIG. 2 illustrates a third exemplary wearable automated medication delivery system 200. As part of the wearable automated medication delivery system 200, an electronic device 202 can hang from a necklace or lanyard hung around a user's neck. Alternatively, the electronic device 202 can be a wearable patch. The electronic device 202 can operate and provide the functionality of the electronic device 106. That is, the electronic device 202 can include some or all of the features described above with reference to the electronic device 106 of FIG. 1A

Each of the wearable automated medication delivery systems 100, 150, and 200 described in relation to FIGS. 1A, 1B, and 2 can be part of a diabetes management system. Such a diabetes management system can monitor a user's glucose levels (as well as other physical attributes of a person) and can determine appropriate levels of insulin to provide a user over time. The appropriate levels of insulin (e.g., in terms of dosages and delivery times) can be adjusted over time based on the user's glucose levels or other physical conditions. The insulin to provide a user can be determined using an "artificial pancreas" algorithm. The algorithm can be implemented by a controller that executes instructions stored in a memory. The controller can determine the amount of insulin to provide based on received sensor data (e.g., glucose levels of the user). The controller can then instruct the medical device 102 of the automated medication delivery systems 100, 150, and 200 to automatically deliver the determined amount of insulin to a user.

The controller for determining the delivery of insulin to the user, any sensor used for collecting and providing data to the controller, and any device providing monitoring output information and capable of receiving user input information can be distributed in any manner across any number of devices. In various embodiments, a glucose sensor (e.g., the sensor 108) is provided as a separate device from a wearable insulin pump (e.g., the medical device 102). In various embodiments, a glucose sensor (e.g., the sensor 108) is provided as part of a wearable insulin pump (e.g., the medical device 102). In various embodiments, the controller for determining the delivery of insulin to the user (e.g., the controller for executing the "artificial pancreas" algorithm) can be provided within a wearable insulin pump (e.g., the medical device 102). In various embodiments, the controller for determining the delivery of insulin to the user (e.g., the controller for executing the "artificial pancreas" algorithm) can be provided in a separate electronic device (e.g., the electronic device 106, the electronic device 202, the local device 116, or the remote device 112).

In various embodiments, any device or component forming a part of a diabetes management systems provided by the wearable automated medication delivery systems 100, 150, and 200 can communicate wirelessly with any other device or component of the system. Any type of wireless link can be used based on any known wireless standard or protocol. Further, in various embodiments, one or more of the devices or components can communicate with one or more remote severs or computing devices including remote cloud-based server systems to provide further monitoring, backup, storage, and/or processing capabilities. The components shown in the wearable automated medication delivery systems 100, 150, and 200 can communicate directly with one another or can communicate indirectly using a relay or intermediate communication device such as, for example, the electronic device 106 or 202.

In various embodiments, the controller for determining the delivery of insulin to the user (e.g., for executing an "artificial pancreas" algorithm) can be provided as part of an electronic device (e.g., the electronic device 106 or electronic device 202) that is separate from a sensor (e.g., the sensor 108) for monitoring a condition or attribute of the user and separate from a wearable insulin pump (e.g., the medical device 102). Under such a scenario, the sensor 108 can send sensor data (e.g., glucose level data or other user data) to the electronic device 106 or 202. The electronic device 106 or 202 can determine an insulin dose based on the received sensor data. The electronic device 106 or 202 can then communicate the determined dosage to the wearable insulin pump 102. The wearable insulin pump 102 can then automatically provide the dosage to the user without user input. Monitoring data (e.g., glucose level data and/or dosage data) can be provided to a monitoring device (e.g., the local device 116 or a remote device 112) for storage or review (e.g., presentation of current or past data related to delivery of the insulin to the user).

In various embodiments, the controller for determining the delivery of insulin to the user (e.g., for executing an "artificial pancreas" algorithm) can be provided as part of the wearable insulin pump (e.g., the medical device 102). Under such a scenario, the sensor 108 can send sensor data (e.g., glucose level data or other user data) to the wearable insulin pump 102. The wearable insulin pump 102 can determine an insulin dose based on the received sensor data. The wearable insulin pump 102 can then automatically provide the dosage to the user without user input. Monitoring data (e.g., glucose level data and/or dosage data) can be provided to a monitoring device (e.g., the local device 116 or a remote device 112) for storage or review (e.g., presentation of current or past data related to delivery of the insulin to the user). Under this scenario, the wearable insulin pump 102 (which can operate as a drug delivery device) can include a communications interface built-in to the wearable insulin pump 102 to provide wireless communication capabilities. Alternatively, an add-on device can be coupled to the wearable insulin pump 102 (e.g., an attachable device) to provide a wireless communication interface and wireless communication capabilities to the wearable insulin pump 102.

In various embodiments, the controller for determining the delivery of insulin to the user (e.g., for executing an "artificial pancreas" algorithm) can be provided as part of the wearable insulin pump (e.g., the medical device 102). Further, the sensor 108 can be provided as part of the wearable insulin pump 102. That is, the sensor 108 can be embedded within the wearable insulin pump 102. Under such a scenario, the sensor 108 can send sensor data (e.g., glucose level data or other user data) to the wearable insulin pump 102. The wearable insulin pump 102 can determine an insulin dose based on the received sensor data. The wearable insulin pump 102 can then automatically provide the dosage to the user without user input. Monitoring data (e.g., glucose level data and/or dosage data) can be provided to a monitoring device (e.g., the local device 116 or a remote device 112) for storage or review (e.g., presentation of current or past data related to delivery of the insulin to the user).

In various embodiments, the controller for determining the delivery of insulin to the user (e.g., for executing an "artificial pancreas" algorithm) can be provided as part of the local electronic device 116. For example, the local electronic device 116 can be a mobile device or a cellphone. The cellphone 116 can include an app for determining insulin delivery to the user. Under such a scenario, the sensor 108 can send sensor data (e.g., glucose level data or other user data) to the cellphone 116 (e.g., directly or indirectly using the electronic device 106 or 202 as a relay). The cellphone 116 can determine an insulin dose based on the received sensor data. The cellphone 116 can communicate the insulin dosage information to the wearable insulin pump 102. The cellphone 116 can communicate with the wearable insulin pump 102 directly or indirectly—for example, indirectly by way of the electronic device 106 or 202. After receiving the dosage information, the wearable insulin pump 102 can provide the dosage to the user. Monitoring data (e.g., glucose level data and/or dosage data) can be provided to a monitoring device (e.g., the local device 116 or a remote device 112) for storage or review (e.g., presentation of current or past data related to delivery of the insulin to the user). As an alternative to a cellphone, the local device 116 can be a dedicated handheld electronic computing device that does not include all of the capabilities of a cellphone (e.g., does not provide an Internet connection or cellular communications interface).

When dosage information is generated and/or provided from the cellphone 116, user input can be required before the wearable insulin pump 102 is allowed to provide the dosage. For example, a user may be required to confirm a command to provide a dosage before the dosage is provided. The wearable insulin pump 102 or the electronic device 106 can include an output device for alerting the user that user confirmation is requested. The alert can be alarm provided visually, audibly, or by other means (e.g., such as vibrating). The wearable insulin pump 102 or the electronic device 106 can further include a user input device for receiving a confirmation input from the user. For example, the user input can be provided by tapping or pressing a button or by receiving an input using an accelerometer provided on the wearable insulin pump 102 or the electronic device 106. This confirmation requirement can represent a cybersecurity measure for the safety of the user.

In various embodiments, the user can be required to provide a confirmation input within a predetermined amount of time after the alarm is provided. If the confirmation is not received within the predetermined amount of time, then the delivery of the insulin to the user can be blocked. Alternatively, if the confirmation is received within the predetermined amount of time, then delivery can be provided as planned. The alarm or alert can indicate receipt of an instruction relating to delivery of the insulin to the user. The confirmation can protect the user from erroneously scheduled insulin delivery to the user. In various embodiments, when a dedicated handled electronic device is used rather than a cellphone for the local device, such confirmation requirements may not be implemented as the security risk to the user is reduced.

In various embodiments, the electronic device 106 can be provided to include the controller for determining medication dosages and times and/or for providing communications between one or more other components of the systems 100, 150, and 200. In various other embodiments, the electronic device 106 is not necessarily present when the controller for determining medication dosages and times can be housed in another component of the systems 100, 150, and 200 and/or when the other system components can communicate without using the electronic device 106 as an intermediary.

Figure 3A:
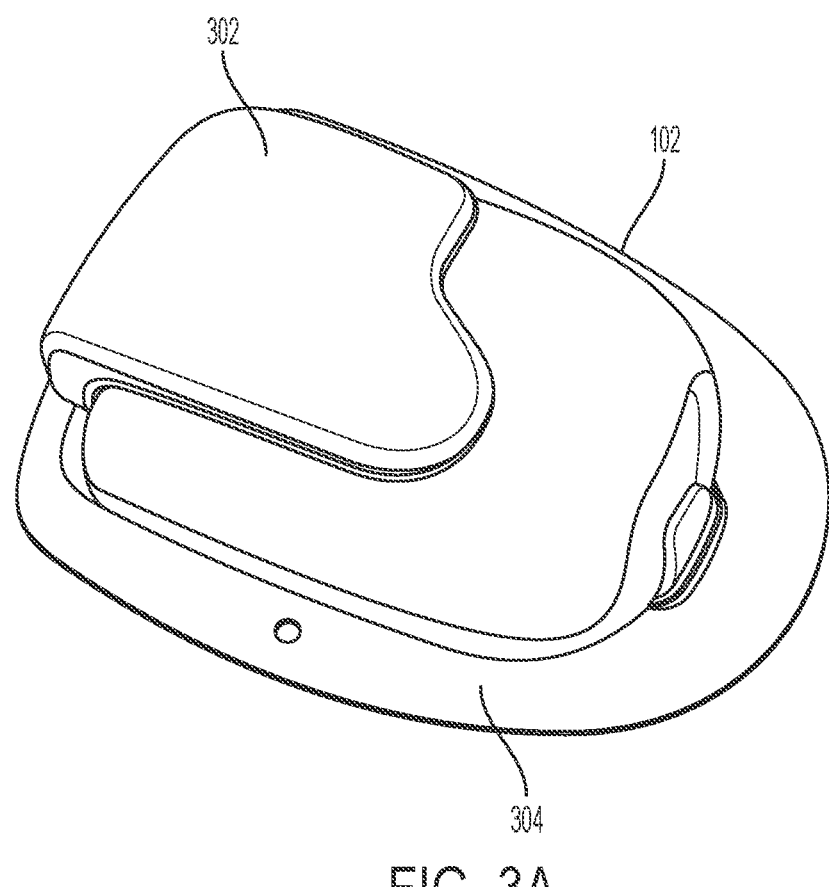
FIGS. 3A and 3B illustrate first and second views of a medical device depicted in FIGS. 1A, 1B, and 2.
Figure 3B:
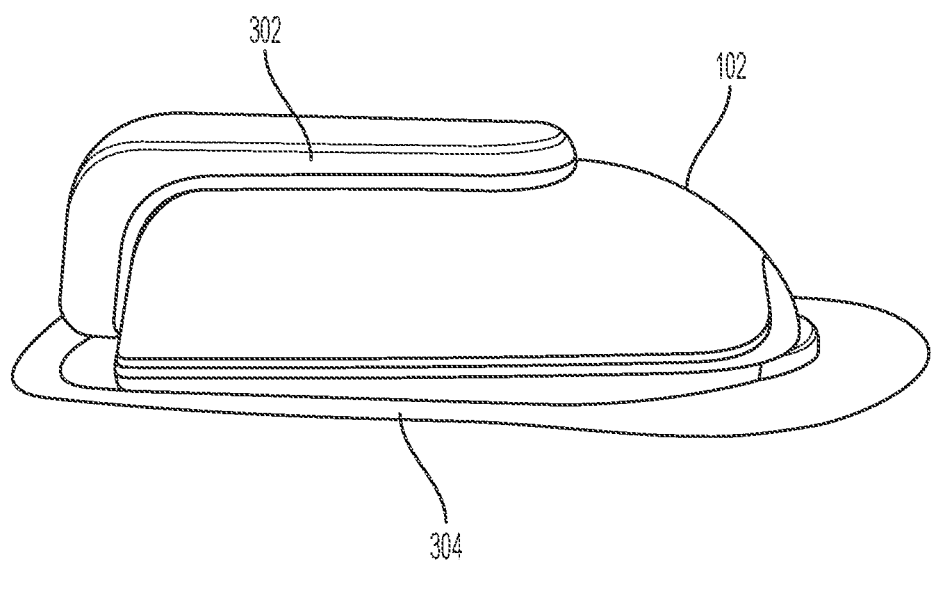

FIGS. 3A and 3B illustrate first and second views of the medical device 102. As shown in FIGS. 3A and 3B, the medical device 102 can include an electronics module 302 that is attached or coupled to the medical device 102. Further, the medical device 102 can include a pad or other surface 304 for adhering to the user. The pad 304 can be coupled to a portion of the medical device 102. The pad 304 can include an adhesive that can be used to attach the medical device 102 to the user.

The attached module 302 can include some or all of the features described above with reference to the electronic device 106 of FIG. 1A. In various embodiments, the module 302 can include a transceiver to enable the medical device 102 to wirelessly communicate with any other device or component depicted in FIG. 1A, 1B, or 2. The module 302 and the medical device 102 can communicate over any known wireless or wired communication standard or protocol. In some embodiments, for example, near-field communication is used for communication between the medical device 102 and the module 302. In other embodiments, a wired connection, such as a universal serial bus connection, is used for communication between the medical device 102 and the module 302.

The electronics module 302 may be removably attached to the medical device 102 so that the electronics module 302 may be used with a plurality of medical devices 102. The electronics module 302 may be sealed and waterproof. The electronics module 302 may have a battery that can be rechargeable using wireless charging.

In various embodiments, the medical device 102 described herein includes a user-input device and/or a user-output device. The user-input device can be a button disposed on the device 102, an acceleration sensor for sensing motion of the medical device 102, or any other such input device. The user-output device may be a speaker for playing sound, a vibration generator (e.g., a motorized gear with an offset center of gravity) for creating vibrations, metal terminals for delivering an electric shock to the body of the person, a visual display and/or one or more lights for providing a visual alarm, or any other such output device.

In various embodiments, when a command is received at the medical device 102 from the electronic device 106, the electronic device 202, or from the local electronic device 116, an action associated with the command (e.g., delivery of a bolus) is not carried out until input is received from the user. The input may include pressing the button on the medical device 102, shaking the medical device 102 (as sensed by the acceleration sensor), tapping the medical device 102 one or more times (as sensed by the acceleration sensor), scanning an RFID or NFC tag, keycard, or fob, or any other such input. If an input is not received within a certain amount of time (e.g., 30 seconds, one minute, two minutes, or any other amount of time), the medical device 102 may not carry out the action. That is, a determined insulin dose may not be delivered. In some embodiments, the output device alerts the person to the arrival of the command at the medical device 102 by, for example, sounding an alarm, vibrating, or providing a visual signal. The output device may similarly alert the user after execution of the action and/or if the action is cancelled due to lack of user input.

Figure 4:
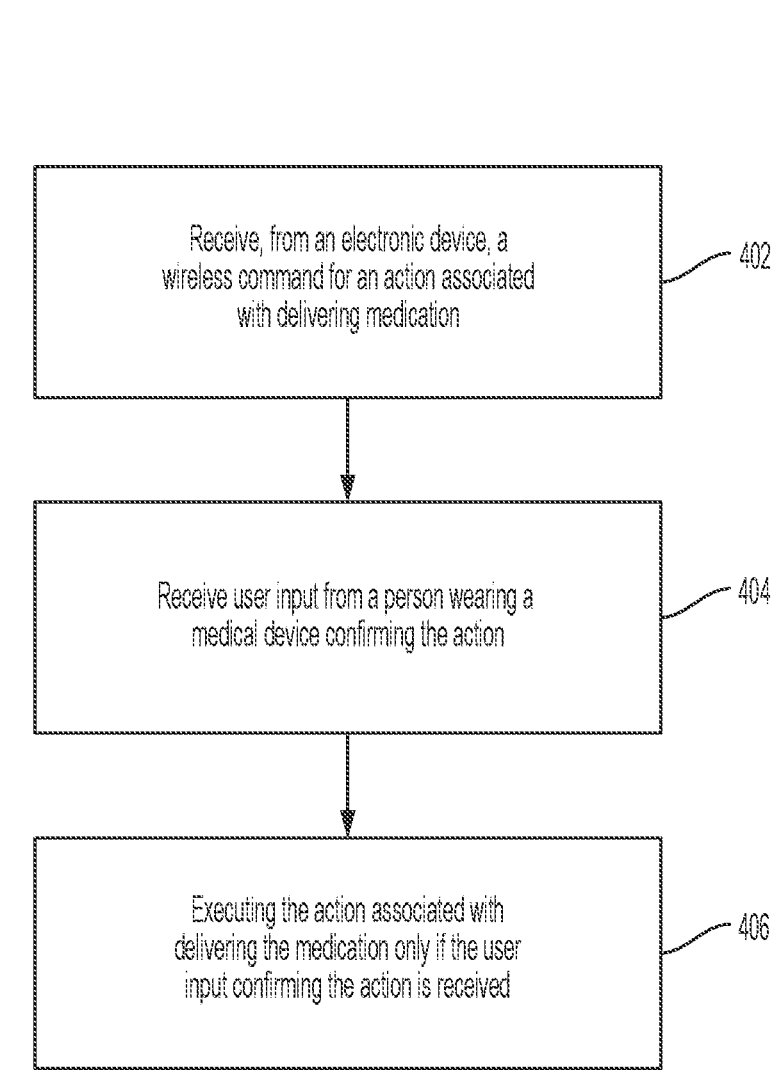
FIG. 4 illustrates a method for dispensing a medication with a wearable drug delivery device.

FIG. 4 illustrates a flowchart 400 of a method for dispensing a medication with a wearable medical device in accordance with the techniques described herein. In a first step 402, a wireless command for an action associated with delivering medication is received from an electronic device. In a second step 404, user input is received from a person wearing the medical device confirming the action. In a third step 406, the action associated with delivering the medication is executed only if the user input confirming the action is received.

The method shown in FIG. 4 can be implemented in various embodiments that require a user to confirm an action prior to any medication dosage being delivered to the user. As an example, the method of FIG. 4 can be implemented when a cellphone 116 is used to determine the dosage to provide to a user (e.g., the cellphone 116 includes a controller that executes an "artificial pancreas" algorithm) and the determined dosage is provided to the wearable insulin pump 102 directly from the cellphone 116 or by way of the electronic device 106 or 202. In various other embodiments described herein, insulin dosages can be provided entirely automatically without user input.

Figure 5:
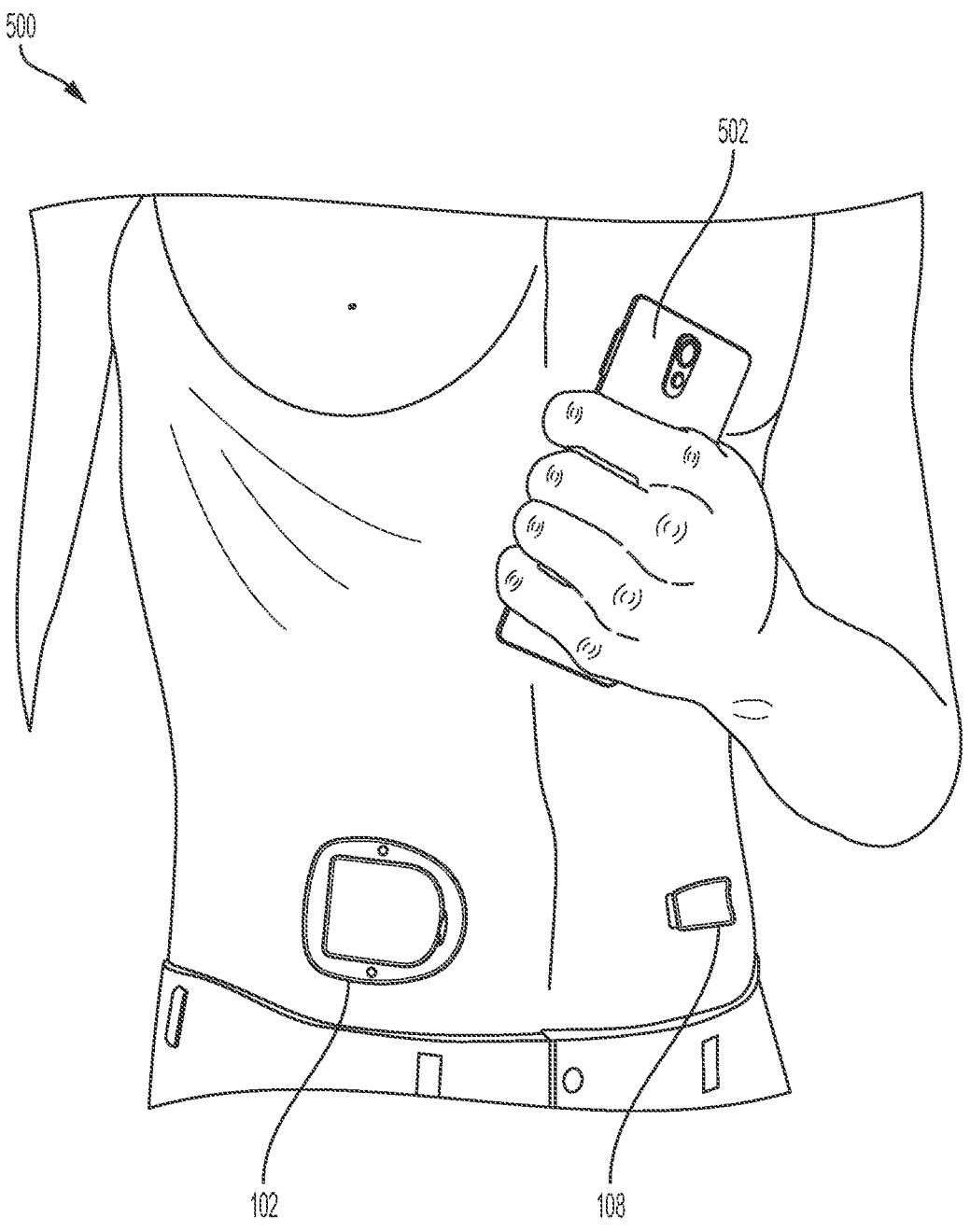
FIG. 5 illustrates a fourth exemplary wearable automated medication delivery system.

FIG. 5 illustrates an exemplary wearable automated medication delivery system 500. The wearable automated medication delivery system 500 can include the wearable insulin delivery device 102, the CGM sensor 108, and a handheld electronic computing device 502. The handheld electronic computing device 502 can be a mobile device or cellphone or can be a dedicated custom electronic device. The wearable insulin delivery device 102 and the CGM sensor 108 can each be directly coupled to a user.

The CGM sensor 108 can provide sensor data to the wearable insulin delivery device 102 and/or the handheld electronic computing device 502. The handheld electronic computing device 502 can include a controller or processor and a memory. The memory can store instructions that can be executed by the controller or processor. The instructions can implement an "artificial pancreas" algorithm. In general, the handheld electronic computing device 502 can include a controller for determining a delivery of insulin to the user (e.g., in terms of dosage amounts and times) based on data from the sensor 108 and providing a corresponding instruction regarding the determined delivery of the insulin to the wearable insulin delivery device 102.

In various embodiments, as mentioned above, the sensor 108 can be provided as part of or embedded within the wearable insulin delivery device 102. Additionally, in various embodiments, as mentioned above, the system 500 can include an intermediate wireless device (e.g., the electronic device 106 or 202) that can relay information wirelessly between the devices depicted in FIG. 5.

In general, the system 500 can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 502 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks.

Figure 6A:
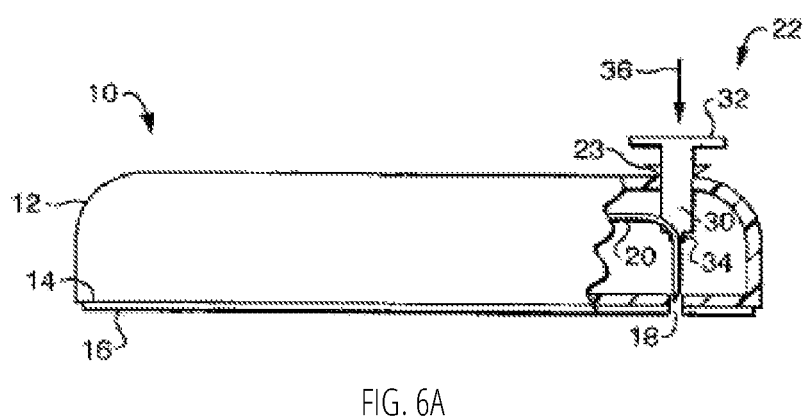
FIGS. 6A-6C are various views of one embodiment of a medical device in accordance with the disclosed subject matter.
Figure 6B:
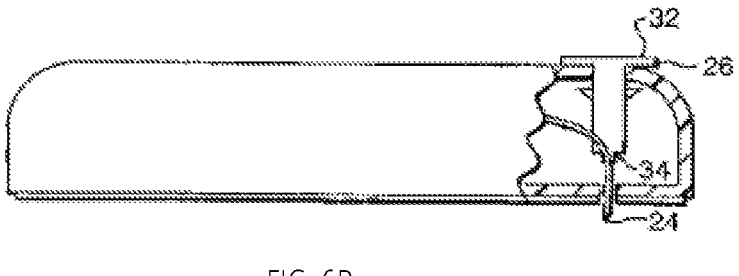
Figure 6C:
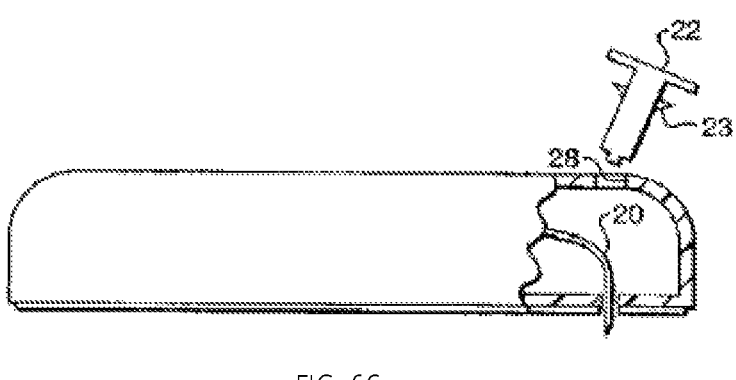

Referring now to FIGS. 6A-6C, an embodiment of the medical device may include a housing 12 for containing the reservoir and other control devices. The footprint of the housing 12 may be square, rectangular, oval or other geometry, depending on the size requirements for containing the reservoir and other control elements as well as the comfort requirements of the user. The housing 12 may include a first wall 14 having, for example, an adhesive material 16 attached thereto for enabling the housing 12 to be adhered to the skin of the user, thereby facilitating secured delivery of fluid to the person. While, in tone embodiment, an attachment mechanism, as shown in FIG. 6A, may be an adhesive tape attached to the first wall 14 of the housing 12, any manner of securing the housing 12 to the user, such as simply taping the housing 12 to the skin of the user, or securing the housing to the user using a strap or other similar device may be used.

The housing 12 may further include an exit port 18, disposed in the first wall 14, for enabling cannula 20 which, in this embodiment, is in the form of a rigid hollow needle having a penetrating portion 24, such as a sharpened point of the cannula 20 for penetrating the skin of the user upon deployment of the cannula as described below. A plunger device 22 may include a body portion 30 which extends through an aperture 28 in a second wall of the housing 12, a head portion 32 and a cannula engagement portion 34 which maintains a frictional engagement with the cannula 20 when the cannula 20 is in the predeployment stage, or first position, shown in FIG. 6A. Plunger device 22 may further include one or more flanges 23 disposed along the body portion 30 thereof. As shown in FIG. 6A, flanges 23 are initially exterior to the housing 12 in the predeployment stage and may cause the plunger device 22 to have a diameter at the point of the flanges 23 which may be greater than the diameter of the aperture 28 of the housing 12.

After the housing 12 has been attached to the user, the cannula may be deployed into the skin of the user by applying manual pressure to the head 32 of the plunger device 22 in the direction shown by arrow 36 of FIG. 6A. Since the flanges 23 may cause the body portion 30 to have a larger diameter at the point of the flanges 23 than the diameter of the aperture 28, a specific force may be required to compress the flanges to a point where they will pass through the aperture 28. This force, once applied, may be great enough to cause the plunger device 22 to force the cannula through the exit port 18 of the first wall 14 and into the skin of the user, such as is shown in FIG. 6B.

The head 32 of plunger device 22 is formed such that when the plunger device is in the deployed stage, or second position, such as shown in FIG. 6B, a peripheral edge 26 of the head portion 32 is disposed relative to the housing 12 so as to expose an underside of the head 32 along the edge 26 for facilitating the removal of the plunger device 22 by prying the plunger device 22 away from the housing 12 upon the application of pressure to the underside of the head portion 32. Cannula engagement portion 34 of the plunger device 22 may be constructed to enable the plunger to force the cannula through the exit port 18 and into the skin of the user, while allowing the plunger device 22 to be removed from the housing 12 such as is shown in FIG. 6C and allowing the cannula 20 to remain in the deployed position shown in FIG. 6C. Once the cannula 20 is deployed into the skin of the user, fluid delivery may be commenced.

Figure 7A:
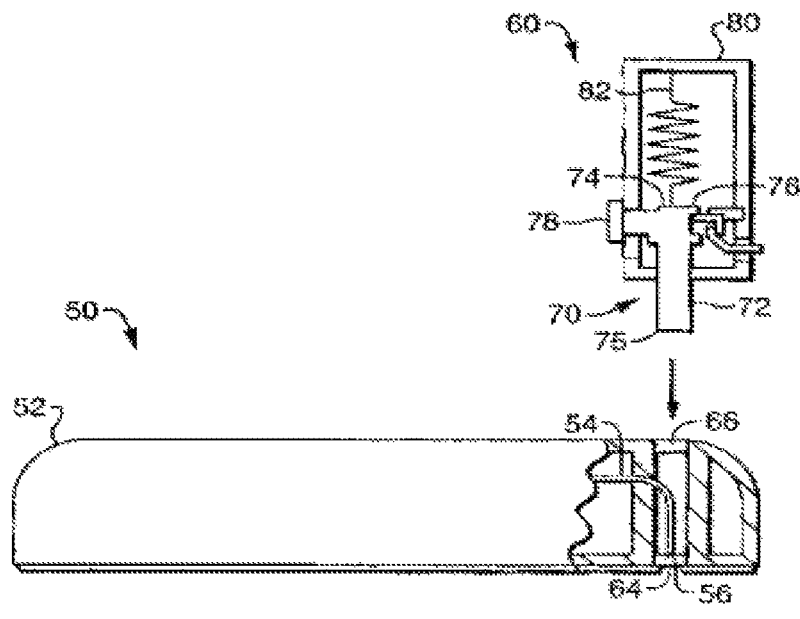
FIGS. 7A-7D are various views of another embodiment of a medical device in accordance with the disclosed subject matter.
Figure 7B:
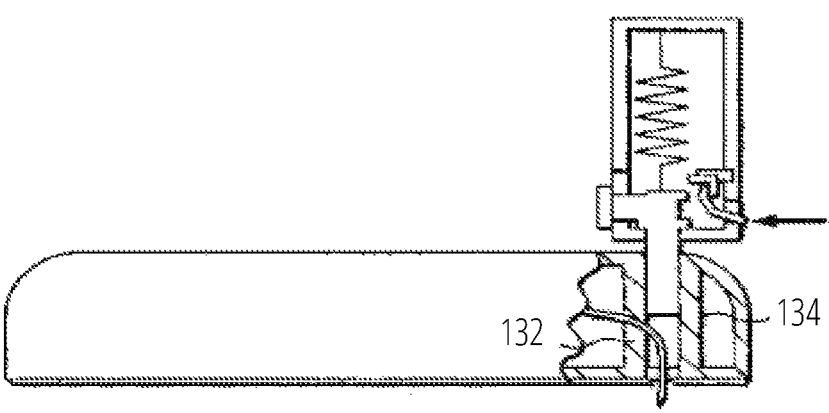
Figures 7C, 7D:
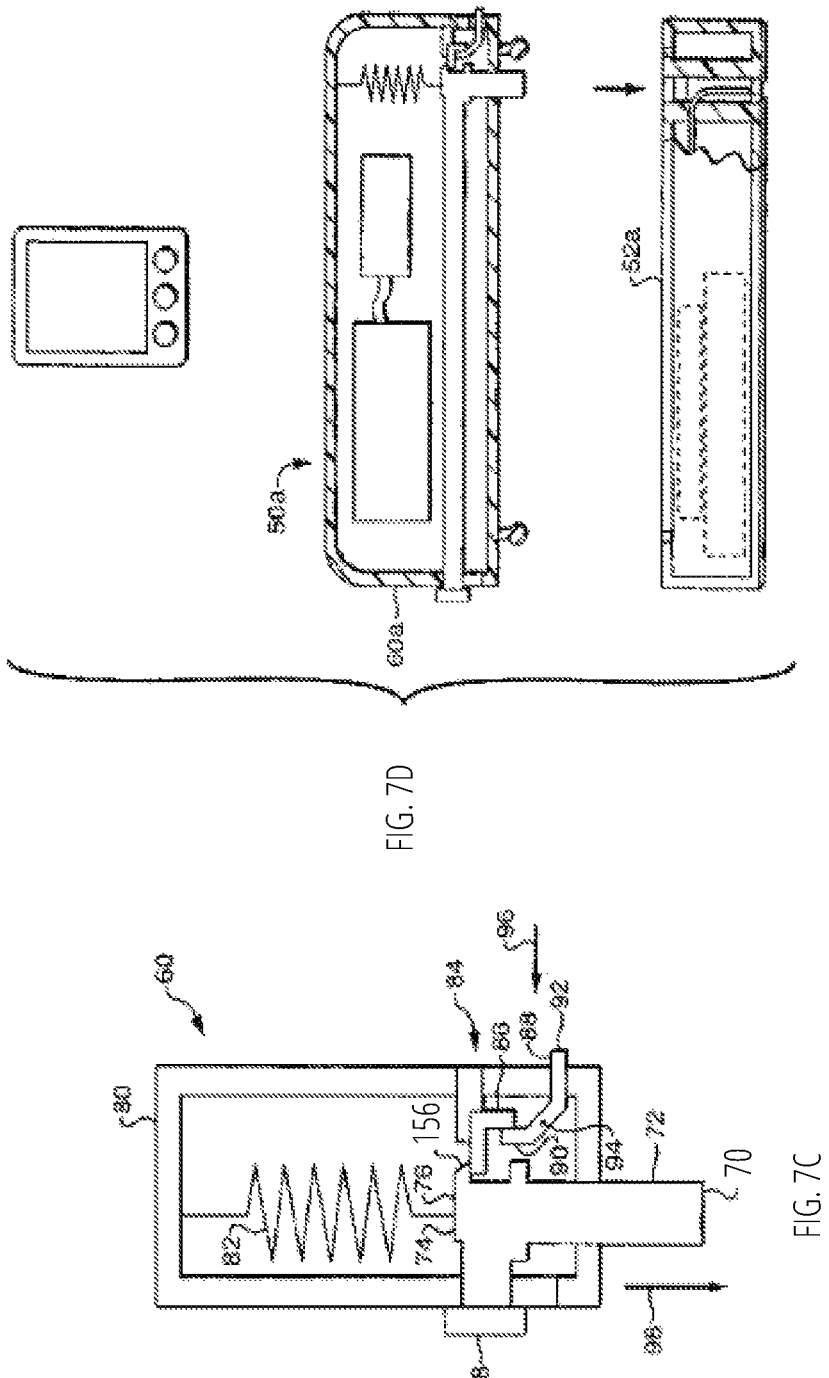

Referring now to FIGS. 7A and 7B, another embodiment of a medical device 50 may include a housing 52 including a cannula 54 having a penetrating member 56 at a distal end thereof. The medical device 50 further may include a discrete injection actuator device 60. As shown in FIG. 7A, housing 52 may include an exit port 64 disposed to enable the cannula 54 to be deployed therethrough, and an actuator port 66 disposed opposite the exit port 64. Injection actuator 60 may include a plunger device 70, including a body portion 72, a head portion 74, a cannula engagement portion 75, a lateral protrusion 76 extending from the body portion 72 proximate the head portion 74 and a reset knob 78. The plunger device 70 may be contained within a secondary housing 80 along with a spring 82 which is in a compressed state when the plunger device 70 is in the predeployment position shown in FIG. 7A. Referring now to FIG. 7C, which is a more detailed view of the injection actuator 60, the operation of the medical device 50 will be described. As is shown in FIG. 7C, actuator 60 may include a latch mechanism 84 including a latch 86 and a deployment lever 88. The latch 86 may be a spring biased such that protrusion 76 is in contact with latch 86, thereby preventing the plunger device 70 from deploying.

Deployment lever 88 may include a first end 90 in contact with latch 86 and a second end 92 which is external to the housing 80. Deployment lever 94 further may include a pivot point 94 at which it is attached to the housing 80, the pivot point 94 enabling the first end 90 of the lever 88 to move in an opposite direction of the second end 92 of the lever 88 when a force is applied to the second end 92 of lever 88 in the direction of arrow 96. Such a force, when applied to the second end 92 of the lever 88 causes the first end 90 of the lever 88 to move in a direction opposite that shown by arrow 96, causing latch 86 to be driven away from the body portion 72 of the plunger device 70, thereby releasing protrusion 76. Once protrusion 76 is released, energy stored in spring 82 is released, causing plunger 70 to be driven in the direction shown by arrow 98.

Referring back to FIGS. 7A and 7B, prior to deployment, the injection actuator 60 is inserted into aperture 66 of housing 52 such that the cannula engagement portion 75 of plunger device 70 is in contact with the cannula 54 while the plunger device 70 is frictionally engaged with sidewalls 132, 134 of housing 52, thereby holding actuator 60 in place relative to the housing 52. Upon actuating the actuator 60 by applying the force to the second end 92 of lever 88, thereby releasing latch 86 from protrusion 76, plunger device 70 applies a force in the direction of arrow 98 to the cannula 54, thereby driving the cannula through the exit port 64 into the skin of the user, as shown in FIG. 7B. At this point, the actuator 60 may be removed from the housing 52 and the reset knob 78 may be pushed in a direction opposite that shown by arrow 98 causing the latch 86 to again engage protrusion 76 with the aid of ramp 156 of protrusion 76, which urges latch 86 away from protrusion 76 while the plunger device 70 is pushed back into the predeployment position shown in FIG. 7C.

FIG. 7D shows an alternative embodiment 50a of the medical device 50, in which an actuator 60a may be used to inject the cannula into the skin of the person, and the actuator may include electronics and wireless receiver separate from a primary housing of the medical device 102 to enable the primary housing 52a of the medical device to have a smaller size and to enable the overall cost of the medical device to be greatly reduced. The actuator 60a is attachable to the housing 52a for deployment of the cannula into the skin of the user and can be removed for use with another medical device. The actuator 60a may include a latch mechanism 84 including a latch 86 and a deployment lever 88. The latch 86 may be spring biased such that a protrusion 76 is in contact with latch 86, thereby preventing the plunger device 70 from deploying.

Figure 8A:
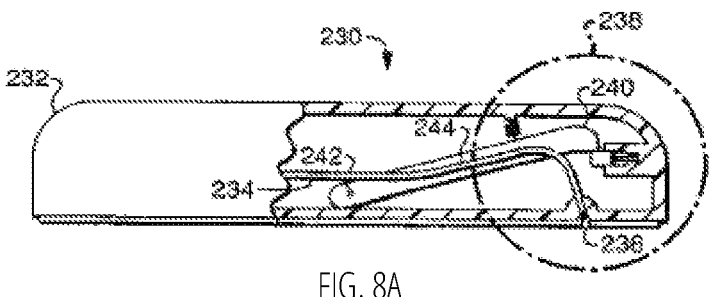
FIGS. 8A-8C are various views of another embodiment of a medical device in accordance with the disclosed subject matter.
Figure 8B:
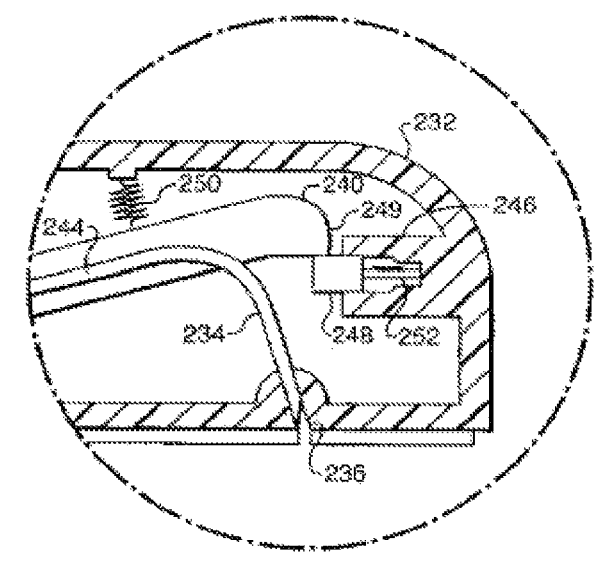
Figure 8C:
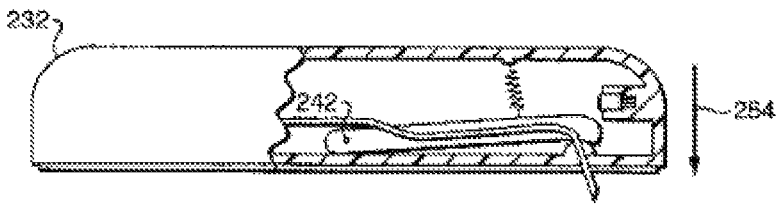

Referring now to FIGS. 8A-8C, a further embodiment 230 of the medical device is described. The medical device 230 may include a housing 232 having an exit port 236. The cannula 234 may be enclosed within the housing 232 in the first position shown in FIG. 8A and in the inset 238 shown in FIG. 8B. The medical device 230 further may include a rod 240 which may be attached to the housing 232 at a pivot point 242 and which may be attached to the cannula 234 along its length at 244. An injection actuation device may include a latch mechanism 246 having a latch 248 which contacts the end 249 of rod 240 for maintaining the rod 240 in the first position shown in FIG. 8A. A biasing spring may be coupled between rod 240 and the housing 232. Biasing spring 250 is in a compressed, energized state when the rod 240 is in the first position, and thus forces the rod against latch 248. The latch mechanism 246 may further include an electrically driven latch actuator 252 which, upon the application of an electrical charge to the latch actuator 252, causes the latch 248 to be moved away from end 249 of rod 240, resulting in the rod 240 and cannula 234 being driven in the direction of arrow 254 under the biasing force of spring 250 to the second position shown in FIG. 8C. Latch actuator 252 receives the electrical charge based on command signals from the local processor, preferably initiated by instructions from a remote processor. In an embodiment, the latch actuator 252 may be a shape memory alloy or polymer which contracts under the influence of an electrical charge. However, other devices may be utilized for the latch actuator 252, such as a piezo electric actuator and a solenoid.

Figure 9A:
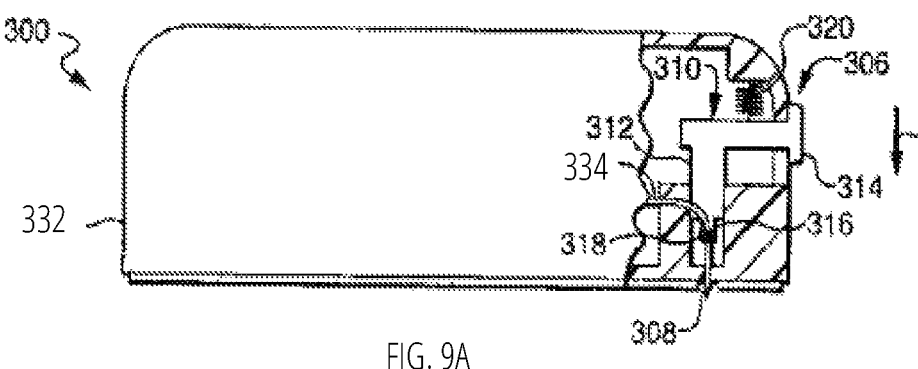
FIGS. 9A-9B are various views of another embodiment of a medical device in accordance with the disclosed subject matter.
Figure 9B:
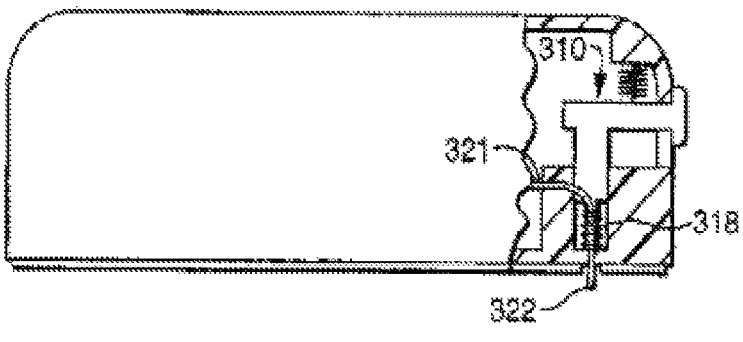

FIGS. 9A and 9B show a further embodiment 300 of the medical device. The medical device 300 may include a housing 332, cannula assembly 334, injection actuator 306 and exit port 308. Injection actuator 306 may include a plunger device 310 having a body portion 312, a deployment knob 314 and a cannula engagement portion 316. A biasing spring 320 may be coupled between the body portion 312 and the housing 332. In the predeployment stage shown in FIG. 9A, the biasing spring is in an unenergized state. Although not explicitly shown in FIG. 9A, the cannula assembly 334 may include a rigid cannula disposed within the lumen of flexible cannula 321. The flexible cannula 321 may include a bellows portion 318 which enables the distal end 322 of the flexible cannula to extend from the housing independent of the rest of the flexible cannula 321. In the predeployment stage shown in FIG. 9A, the bellows portion may be compressed and the distal end 322 of flexible cannula 321 is within the housing 332.

Deployment of the flexible cannula into the user's skin takes place as follows. After the housing is attached to the user, the user or other person pushes knob 314 of the injection actuator 306 in the direction indicated by arrow 324. This causes the cannula assembly 334 to be driven into the skin of the user through exit port 308, as described above. Once the plunger device 310 has reached the end of its travel and both the rigid cannula and the flexible cannula 321 have been injected into the skin of the person, biasing spring 320 may be extended and energized such that when the knob 314 is released, biasing spring 320 deenergizes, causing the cannula assembly 334 to be retracted into the housing 332. However, because of the retention device disposed either on the flexible cannula or within the exit port 308, the distal end 322 of the flexible cannula 321 is retained in the deployed position shown in FIG. 9B and the bellows portion 318 is fully expanded, which enables the rigid cannula to be retracted without also retracting the distal end 322 of the flexible cannula 321. Depending on the particular design of the medical device, in the deployed position, the rigid cannula may be retracted to a position that is the same as its predeployment position, to a position that is between the predeployment position and the deployment position, or to a position that is further away from the deployment position than the predeployment position.

Figure 10A:
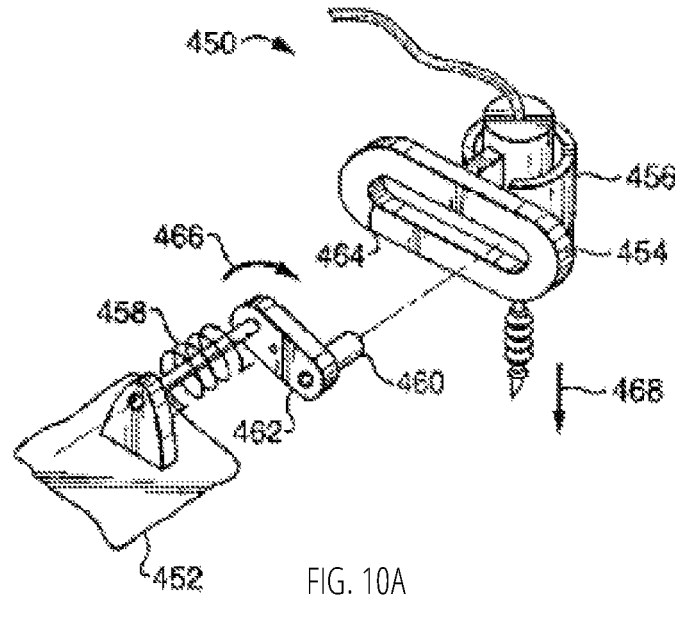
FIGS. 10A-10B are various views of another embodiment of a medical device in accordance with the disclosed subject matter.
Figure 10B:
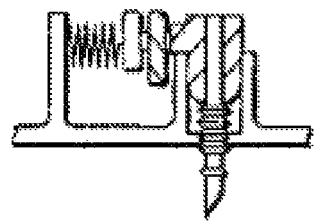

FIGS. 10A and 10B show an embodiment 450 which may include a driving mechanism 452 which is coupled to a force translator 454 which in turn is coupled to cannula assembly 456. In an embodiment, driving mechanism 452 may include a torsion spring which is energized before protrusion 460 of lever arm 462 is inserted into slot 464 of force translator 454. FIG. 10B is a side view of the embodiment 450 in such a configuration. When the torsion spring 458 is released, it lever arm 462 and protrusion 460 to rotate in the direction indicated by arrow 466, causing protrusion 460 to drive the force translator 454 and cannula assembly 456 in the direction indicated by arrow 468 during the first 45 degrees of rotation, thereby injecting the rigid cannula and flexible cannula into the skin of the person, and then to drive the force translator 454 and cannula assembly 456 in the direction opposite that indicated by arrow 468 during the second 45 degrees of rotation, thereby retracting the rigid cannula. The flexible cannula may maintain its deployment position with the aid, for example, of the bellows portion and the retention device.

As discussed above, the wearable insulin delivery device 102 can include one or more user output devices that can be used to provide an alarm, alert, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Further, many of the techniques and embodiments described are not limited to the delivery of insulin but are applicable to the automated delivery of any medication to a user.

The invention claimed is:

1. An automated drug delivery device, comprising:
at least one housing encompassing:
a reservoir configured to contain a medication;
a pump configured to transfer the medication from the reservoir;
a power supply operable to supply power to the pump;
a needle and/or a cannula configured to dispense the medication;
a needle insertion device operable to deploy the needle and/or the cannula into skin of a user;
a receiver configured to receive signals over a wireless link;
a memory configured to store an algorithm; and
a controller, wherein the controller is coupled to the memory, and, when executing the algorithm stored in the memory coupled to the controller, the controller is configured to locally:
receive, via the receiver, sensor data from a glucose sensor positioned on the skin of a user;
determine locally by the controller a size of a dose of medication and at least a change in a time of delivery, a frequency of delivery, or a schedule of future delivery of the dose of the medication based at least in part on the received sensor data; and
cause the pump to deliver medication from the reservoir based on the determined size of the dose of the medication and the at least the change in the time of delivery, the frequency of delivery, or the schedule of future delivery of the dose of the medication.

2. The automated drug delivery device of claim 1, wherein the power supply is a replaceable battery.

3. The automated drug delivery device of claim 1, wherein the needle insertion device comprises:
a latch release mechanism operable to prevent a plunger device from deploying the needle and/or cannula in skin of a user.

4. The automated drug delivery device of claim 3, wherein the latch release mechanism includes:
a latch operable to hold the plunger device from being deployed; and
a deployment lever, wherein the deployment lever is operable, in response to a force, to release the latch holding the plunger device.

5. The automated drug delivery device of claim 1, further comprising:
an adhesive pad attachable to a user.

6. The automated drug delivery device of claim 1, wherein:
the medication is insulin, and
the determined size of the dose of the medication is an insulin dosage amount.

7. The automated drug delivery device of claim 1 wherein the glucose sensor is:
within the drug delivery device, and
configured to determine data related to the user.

8. The automated drug delivery device of claim 1, wherein the controller is further operable to:
determine one or more of:
delivery of a bolus of the medication, a change in a size of future deliveries of the medication, a bolus size, or a bolus delivery time.

9. The automated drug delivery device of claim 1, wherein the needle insertion device is a manual activation device responsive to a manual pressure.

10. The automated drug delivery device of claim 1, wherein the needle insertion device is an electrical activation device responsive to a command from a remote device.

11. A wearable drug delivery system comprising:
a glucose sensor coupled to skin of a user, wherein the sensor is operable to collect sensor data on a physical attribute or condition of the user; and
a wearable medical device coupled to the skin of the user, the wearable medical device including:
a reservoir configured to contain a medication;
a pump configured to transfer the medication from the reservoir;
a power supply operable to supply power to the pump;
a needle and/or cannula configured to dispense the medication;
a needle insertion device operable to deploy the needle and/or the cannula into skin of the user;
a receiver configured to receive signals over a wireless link;
a memory configured to store an algorithm; and
a controller, wherein the controller is coupled to the memory, and, when executing the algorithm stored in memory coupled to the controller, the controller is configured to locally:
receive, via the receiver, the sensor data from the glucose sensor;
determine locally by the controller a size of a dose of medication and at least a change in a time, frequency, or schedule of future delivery of the dose of the medication based at least in part on the received sensor data; and
cause the pump to deliver medication from the reservoir based on the determined size of the dose of the medication and the at least the change in the time of delivery, the frequency of delivery, or the schedule of future delivery of the dose of the medication.

12. The system of claim 11, wherein the controller is further operable to locally:
determine one or more of:
delivery of a bolus of the medication, a change in a size of future deliveries of the medication, a bolus size, or a bolus delivery time.

13. The system of claim 11, wherein:
the medication is insulin.

14. The system of claim 11, wherein the power supply is integrated in the automated drug delivery device.

15. The system of claim 11, wherein the power supply is a replaceable battery.

16. The system of claim 11, further comprising:
a latch release mechanism operable to prevent the needle insertion device from deploying the needle and/or cannula into the skin of the user.

17. The system of claim 16, wherein the latch release mechanism includes:
a latch operable to hold the needle insertion device from being deployed; and
a deployment lever, wherein the deployment lever is operable, in response to a force, to release the latch holding the needle insertion device.

18. The system of claim 11, further comprising:
an adhesive pad attachable to the user.

19. The system of claim 11, wherein the glucose sensor is:
embedded within the wearable medical device, and configured to determine data related to the user.

20. A wearable drug delivery system comprising:
a glucose sensor coupled to skin of a user, wherein the sensor is operable to collect sensor data on a physical attribute or condition of the user; and
a wearable medical device coupled to the skin of the user, the wearable medical device including:
a reservoir configured to contain a medication;
a pump configured to transfer the medication from the reservoir;
a power supply operable to supply power to the pump;
a needle and/or cannula configured to dispense the medication;
a needle insertion device operable to deploy the needle and/or the cannula into skin of the user, wherein the needle insertion device is a manual activation device responsive to a manual pressure, or the needle insertion device is an electrical activation device responsive to a command from a remote device;
a receiver configured to receive signals over a wireless link;
a memory configured to store an algorithm; and
a controller, wherein the controller is coupled to the memory, and, when executing the algorithm stored in memory coupled to the controller, the controller is configured to locally:
receive, via the receiver, the sensor data directly from the glucose sensor;
determine locally on the controller a size of a dose of medication and at least a change in a time, frequency, or schedule of future deliveries of the medication based at least in part on the received sensor data; and
cause the pump to deliver medication from the reservoir based on the determined size of the dose of the medication and the at least the change in the time of delivery, the frequency of delivery, or the schedule of future deliveries of the dose of the medication.

* * * * *